(12) United States Patent
Ramsay et al.

(10) Patent No.: US 8,116,983 B2
(45) Date of Patent: Feb. 14, 2012

(54) DEVICE FOR QUANTITATIVE ANALYSIS OF A DRUG OR METABOLITE PROFILE

(75) Inventors: Steven Lewis Ramsay, Igls (AT); Wolfgang Guggenbichler, Rum (AT); Klaus Michael Weinberger, Mieming (AT); Armin Graber, Innsbruck (AT); Wolfgang Markus Stoeggl, Innsbruck (AT)

(73) Assignee: Biocrates Life Sciences AG, Tirol (AT)

( * ) Notice: Subject to any disclaimer, the term of this patent is extended or adjusted under 35 U.S.C. 154(b) by 1472 days.

(21) Appl. No.: 11/476,657

(22) Filed: Jun. 29, 2006

(65) Prior Publication Data
US 2007/0003965 A1 Jan. 4, 2007

Related U.S. Application Data

(60) Provisional application No. 60/694,984, filed on Jun. 30, 2005, provisional application No. 60/694,983, filed on Jun. 30, 2005.

(51) Int. Cl.
*G01N 33/48* (2006.01)
(52) U.S. Cl. ......................................... 702/19
(58) Field of Classification Search ................. 702/19
See application file for complete search history.

(56) References Cited

U.S. PATENT DOCUMENTS

| | | | |
|---|---|---|---|
| 6,258,605 B1 | 7/2001 | Chace | |
| 6,455,321 B1 | 9/2002 | Chace | |
| 6,627,444 B1 | 9/2003 | Goledzinowski et al. | |
| 2002/0009740 A1 | 1/2002 | Kaddurah-Daouk et al. | |
| 2003/0044799 A1 | 3/2003 | Matson | |
| 2003/0199102 A1 | 10/2003 | Ostrup | |
| 2005/0112635 A1 | 5/2005 | Gentle et al. | |
| 2006/0057554 A1 | 3/2006 | Watling et al. | |

FOREIGN PATENT DOCUMENTS

| | | |
|---|---|---|
| GB | 2 385 918 A | 9/2003 |
| JP | 2005-512061 | 4/2005 |
| JP | 2005-523448 A | 8/2005 |
| JP | 2007-516425 A | 6/2007 |
| JP | 2007-524844 A | 8/2007 |
| WO | WO 96/24062 A1 | 8/1996 |
| WO | WO 00/72019 A2 | 11/2000 |
| WO | WO-03/005628 | 1/2003 |
| WO | WO 03/016861 A2 | 2/2003 |
| WO | WO 03/025212 A2 | 3/2003 |
| WO | WO 03/025212 A3 | 3/2003 |
| WO | WO 03/048784 A2 | 6/2003 |
| WO | WO 03/089908 A1 | 10/2003 |
| WO | WO 2004/101809 A2 | 11/2004 |
| WO | WO 2005/031304 A2 | 4/2005 |

OTHER PUBLICATIONS

Flora et al. "High-Mass Accuracy of Product Ions Produced by SORI-CID Using a Dual Electrospray Ionization Source Coupled with FTICR Mass Spectrometry," Analytical Chemistry (2001) vol. 73, No. 6, pp. 1247-1251.*

Altria "Overview of Capillary Electrophoresis and Capillary Electrochromatography," Journal of Chromatography (1999) vol. 856, pp. 443-463.*

Bayerl et al. "Physical Properties of Single Phospholipid Bilayers Adsorbed to Micro Glass Beads," Biophysical Journal (1990) vol. 58, pp. 357-362.*

Harrigan, G.G. & Goodacre, R. (2003) Metabolic profiling: Its role in biomarker discovery and gene function analysis. Kluwer Academic Publishers, Boston/Dordrecht/London. Chapters 1,4,8,9,10, 11,13 and 17.

Schmidt, C (2004) Journal of the National Cancer Institute, vol. 96, No. 10, pp. 732-734.

Raudys, S. (2001) Statistical and neural classifiers, Springer-Verlag, London. Contents, Chapters 1-6 and Appendices.

Daviss, B. (2005)The Scientist, vol. 19.,"Gowing Pains for Metabolomics", pp. 25-28.

Beecher C., (2003). In Harrigan, G.G., Goodacre, R.(Ed). Metabolic profiling: Its role in biomarker discovery and genge function analysis (pp. 311-319). Kluwer Academic Publishers, Boston/Dordecht/London.

Dunn, W.B. et al. (2005) Analyst, vol. 130, pp. 606-625.

Biomarkers Definitions Working Group. (2001) Clinical Pharmacology and Therapuetics, vol. 69, pp. 89-95.

Stoughton, R.B. & Friend, S.H. (2005) Nature Reviews. Drug Discovery, vol. 4, pp. 345-350.

Morris, M., & Watkins, S.M. (2005). Current Opinion in Chemical Biology., vol. 9, pp. 407-412.

McCandless, S.E. (2004). Primary Care, vol. 31, pp. 583-604.

Roschinger, W. et al. (2003). European Journal of Pediatrics, vol. 162 (Suppl 1), pp. S67-S76.

Strauss, A.W. (2004). J Clin Invest 2004: vol. 113, pp. 354-356.

Kaltashov, I.A. & Eyles, S.J. (2005) Mass spectrometry in biophysics: Conformation and dynamics of biomolecules. Wiley Contents, Chapters 1-11.

Tanaka et. al, (2001)Clinical Chemistry, vol. 47:10, pp. 1829-1835.

Examination Report dated Apr. 26, 2010 issued in corresponding Canadian Patent Application No. 2,608,965.

Notice of Reasons for Rejection mailed Sep. 21, 2010 for Japanese Aplication No. 2008-518727.

International Search Report and Written Opinion of the International Searching Authority dated Feb. 2, 2007 for Application No. PCT/EP2006/006328 (PCT/ISA/220, PCT/ISA/210 and PCT/ISA/237).

Japanese Office Action issued in Japanese Patent Application No. 2008-518727 on Oct. 25, 2011, with English language translation.

* cited by examiner

*Primary Examiner* — Jerry Lin
(74) *Attorney, Agent, or Firm* — Birch, Stewart, Kolasch & Birch, LLP.

(57) ABSTRACT

A device, in particular a sample preparation device for the quantitative analysis of a drug and/or metabolite profile in a biological sample, which includes an insert for such a device being impregnated with at least one internal standard, to the internal standard itself, and to a kit comprising the device. Further, the invention also relates to an apparatus containing the device, and to a method for the quantitative analysis of a drug and/or metabolite profile in a biological sample employing the device.

31 Claims, 10 Drawing Sheets

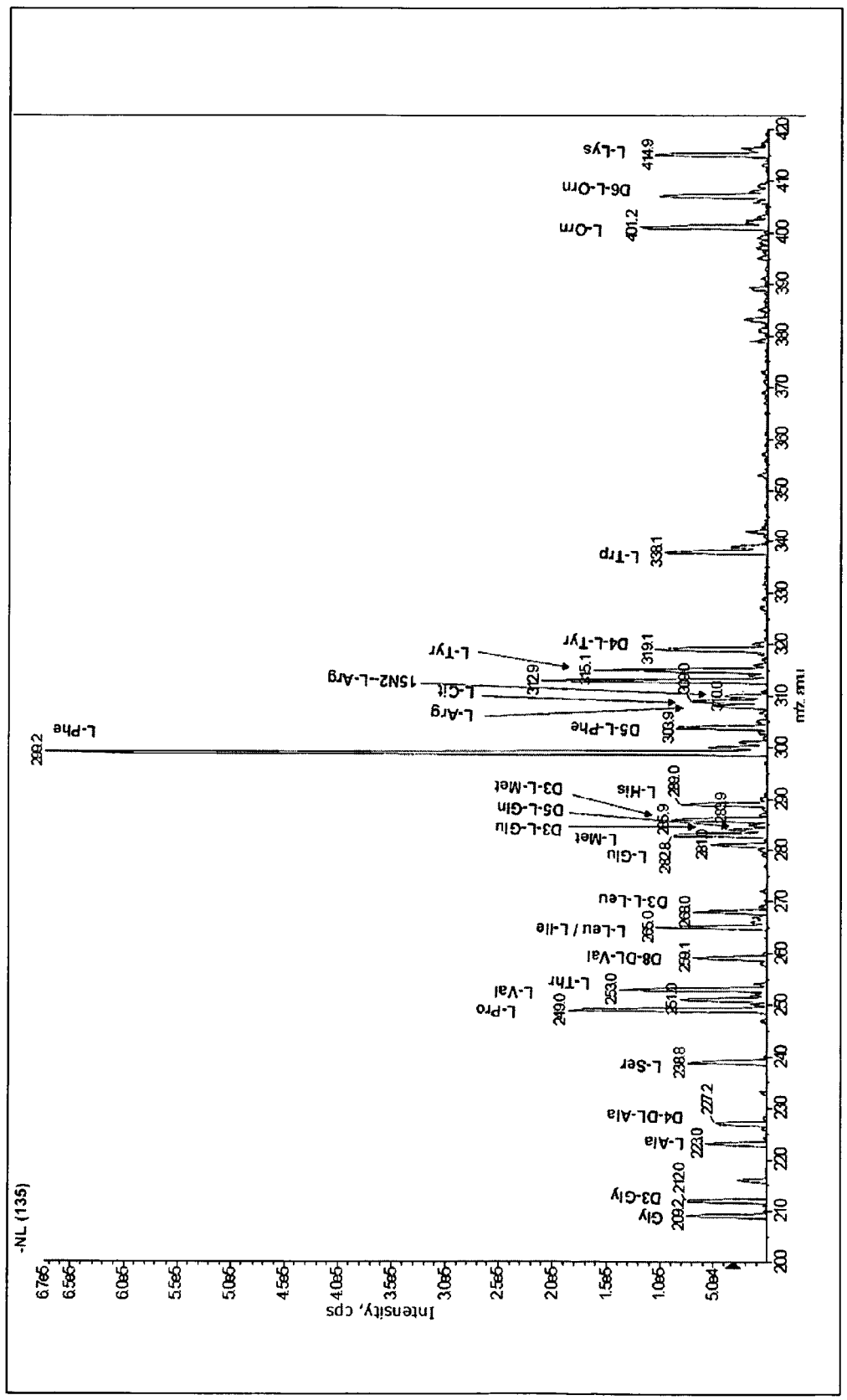
Figure 2. Phenylthiourea derivatives of a selection of amino acid standards and internal standards (stable isotopes)

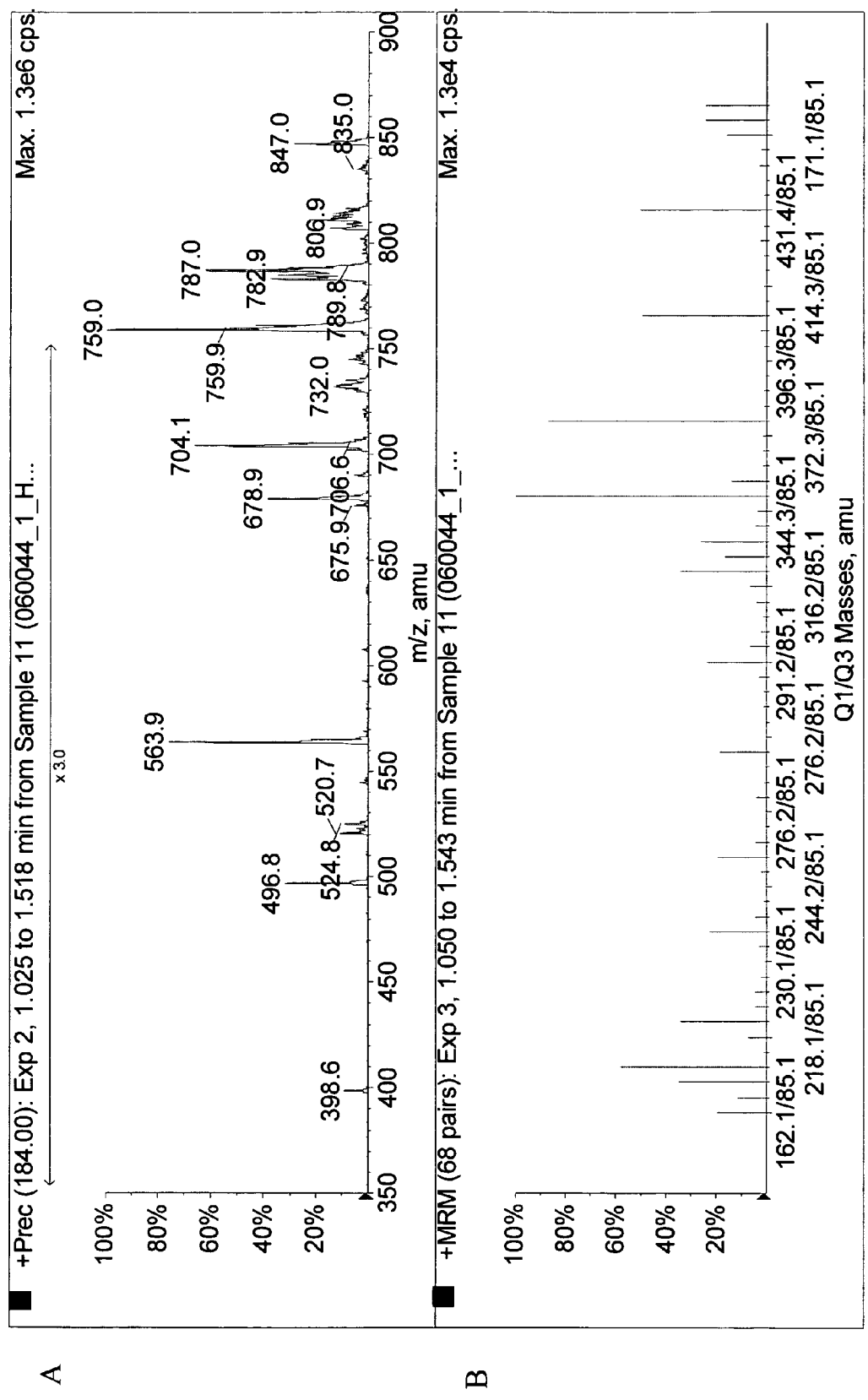
Figure 3. A; shows precursor ion of 184 specific for choline-containing lipids like sphingomyelins and phosphatidylcholines and B; multiple reaction monitoring (MRMs) of individual acylcarnitines, all extracted from plasma

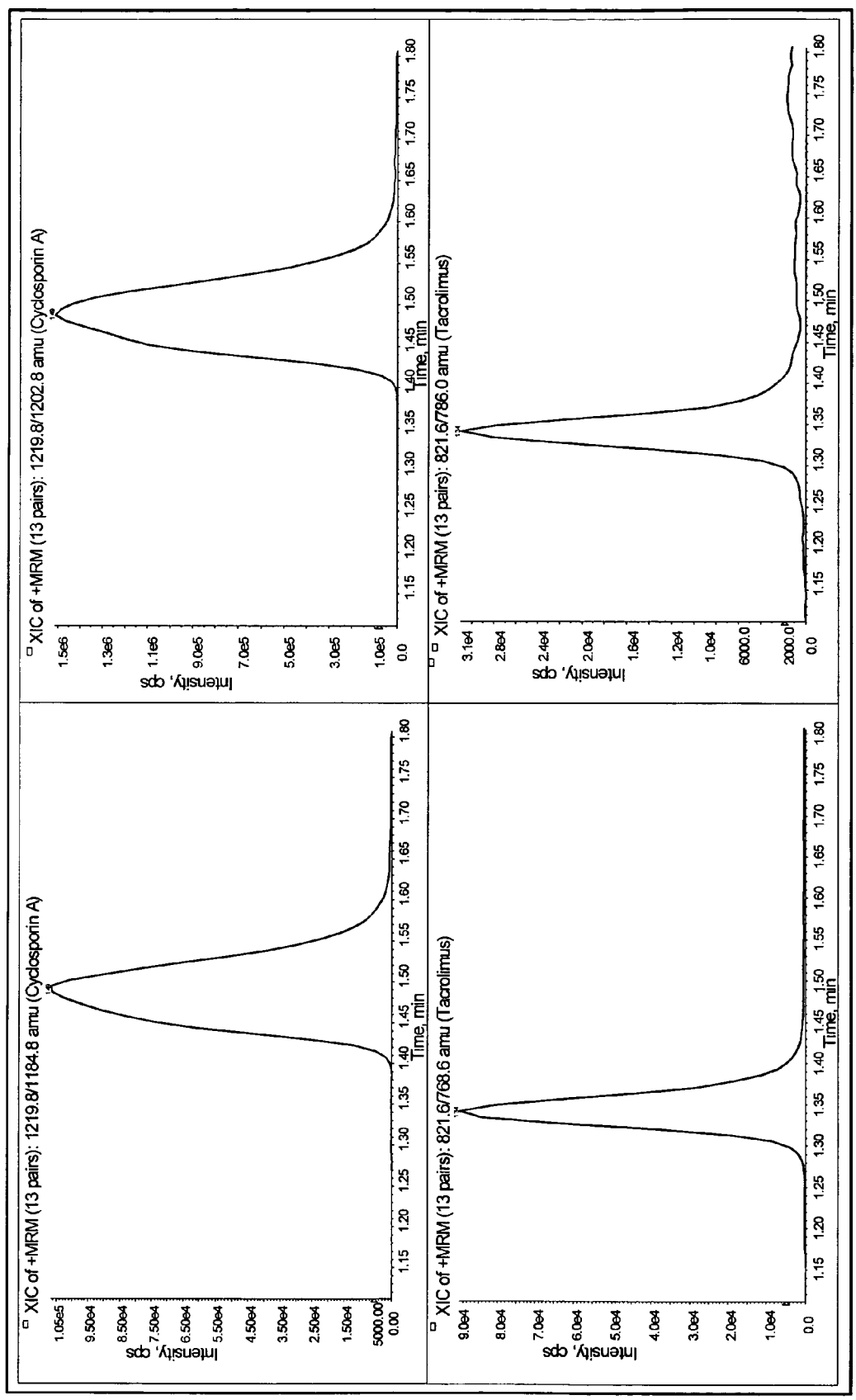
Figure 4a. Multiple MRM transitions of therapeutic drugs Cyclosporin A and Tacrolimus from a quality control blood sample

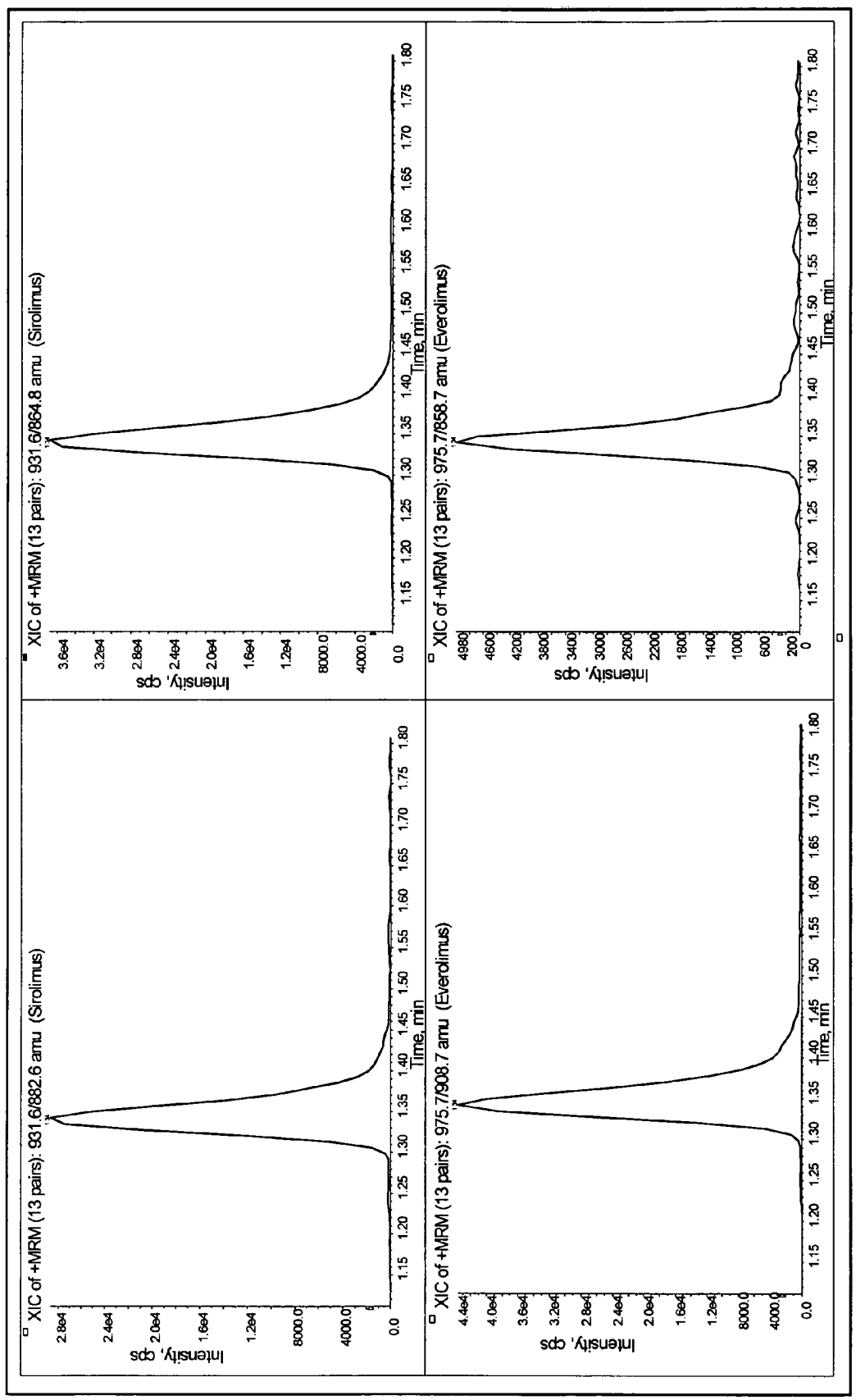
Figure 4b. Multiple MRM transitions of therapeutic drugs Sirolimus and Everolimus from a quality control blood sample

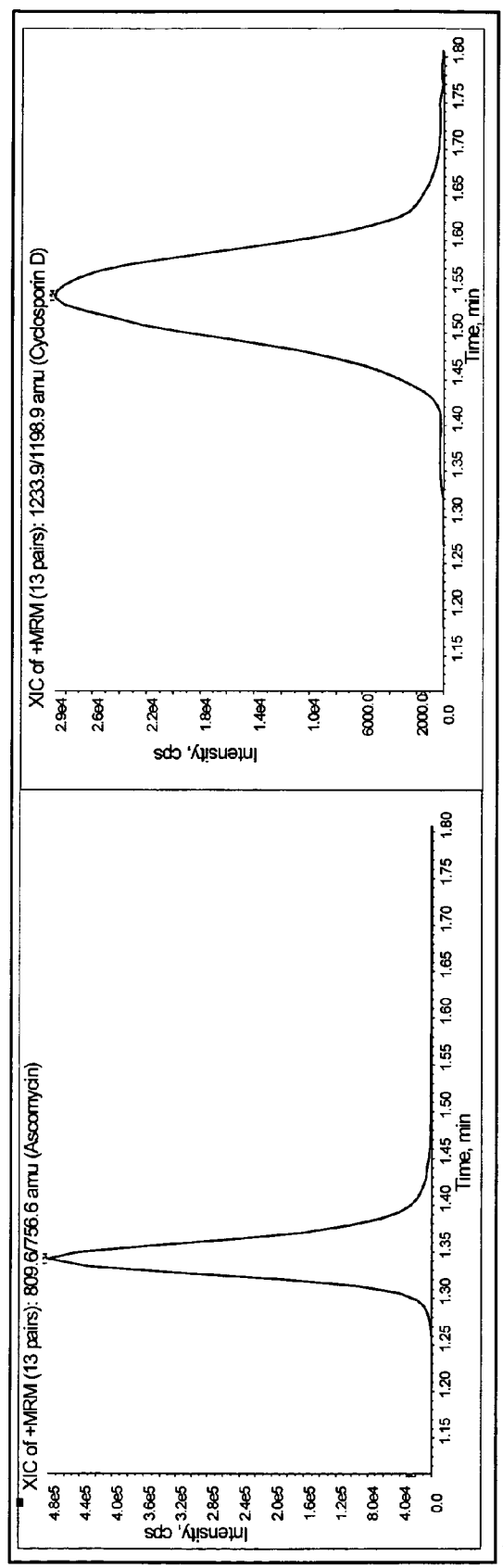
Figure 4c. Multiple MRM transitions of Internal standards Ascomycin and Cyclosporin D from a quality control blood sample

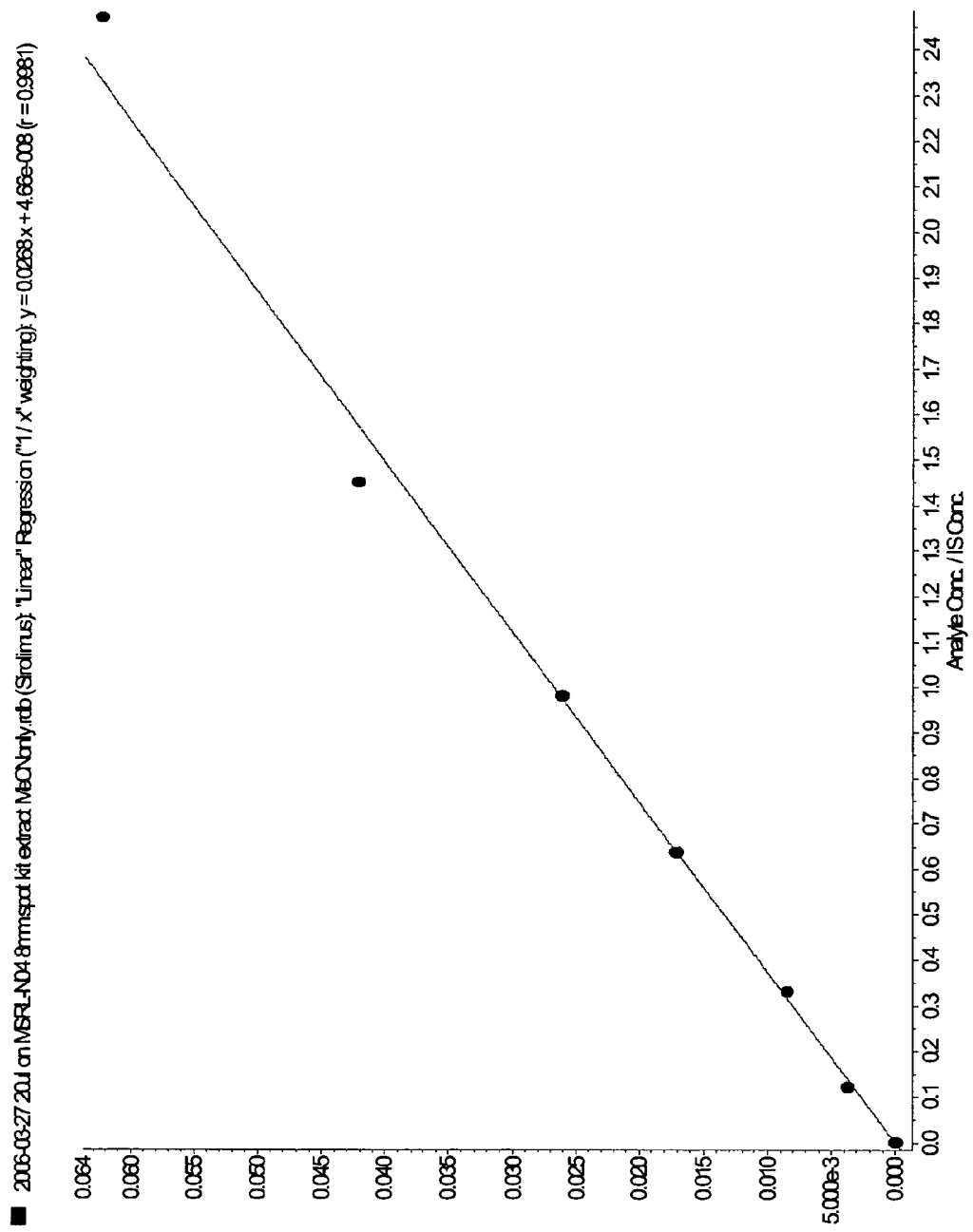
Figure 5. Sirolimus calibration curve (r=0.9981)

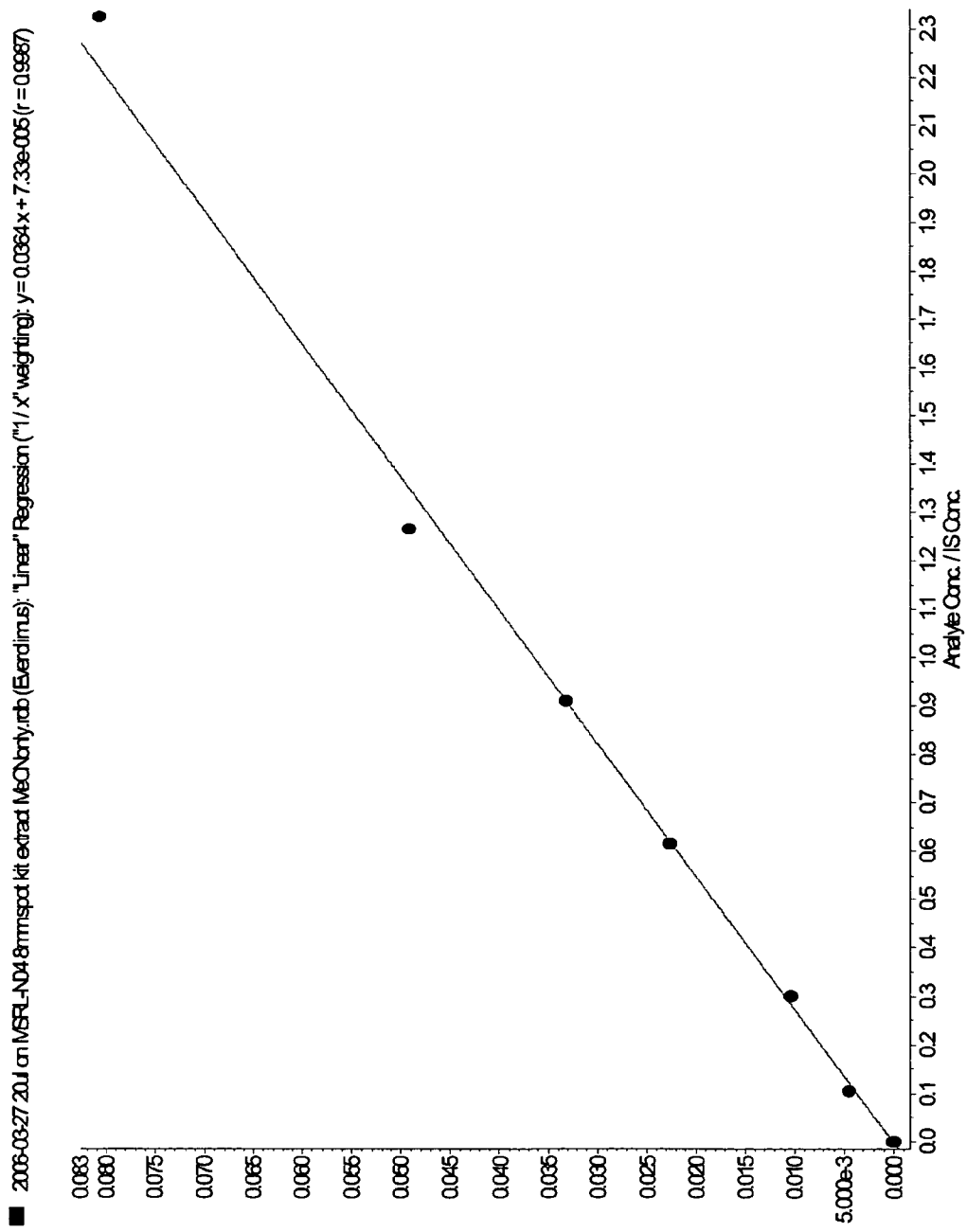
Figure 6. Everolimus calibration curve (r=0.9987)

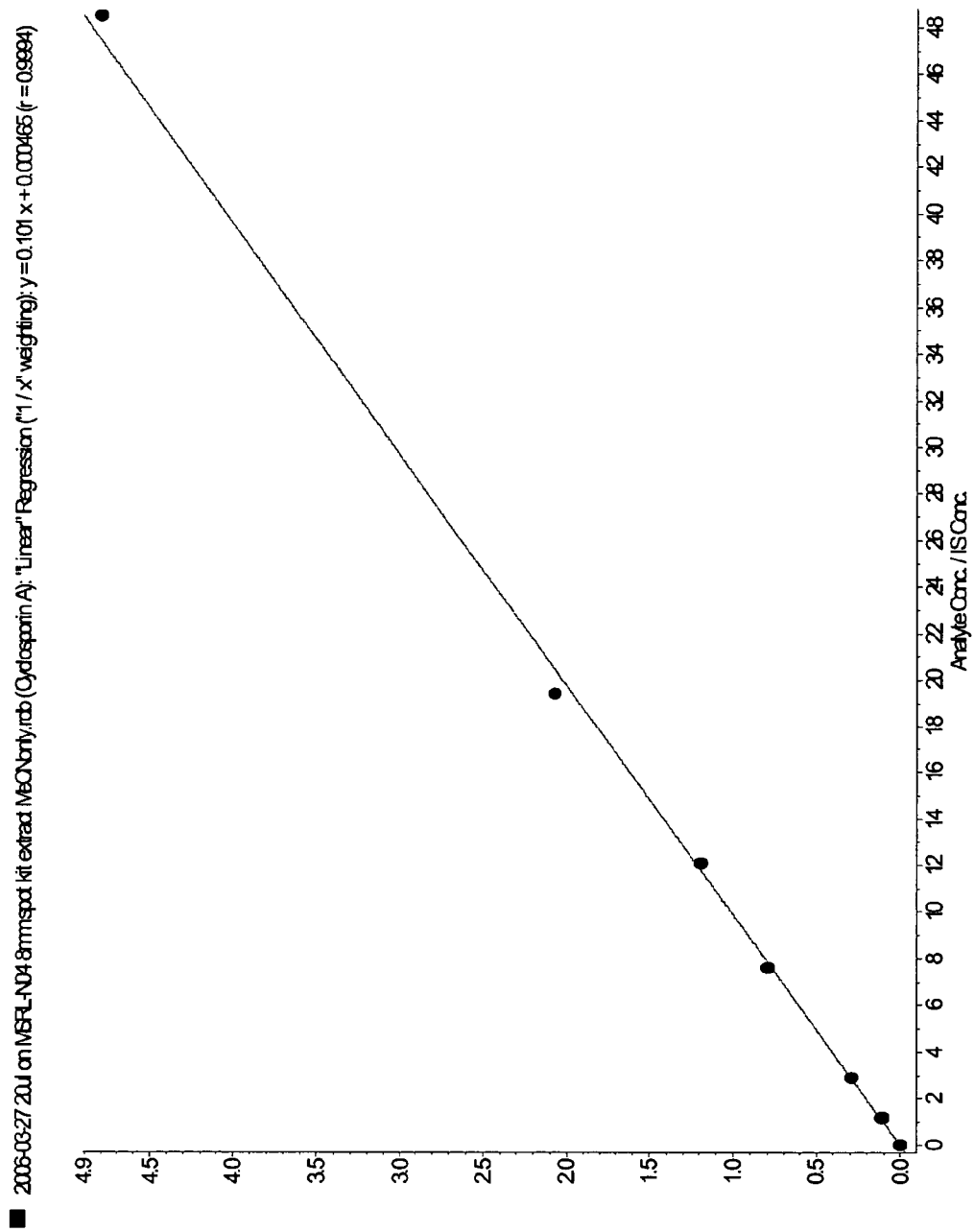
Figure 7. Cyclosporin A (Cyc A) calibration curve (r=0.9994)

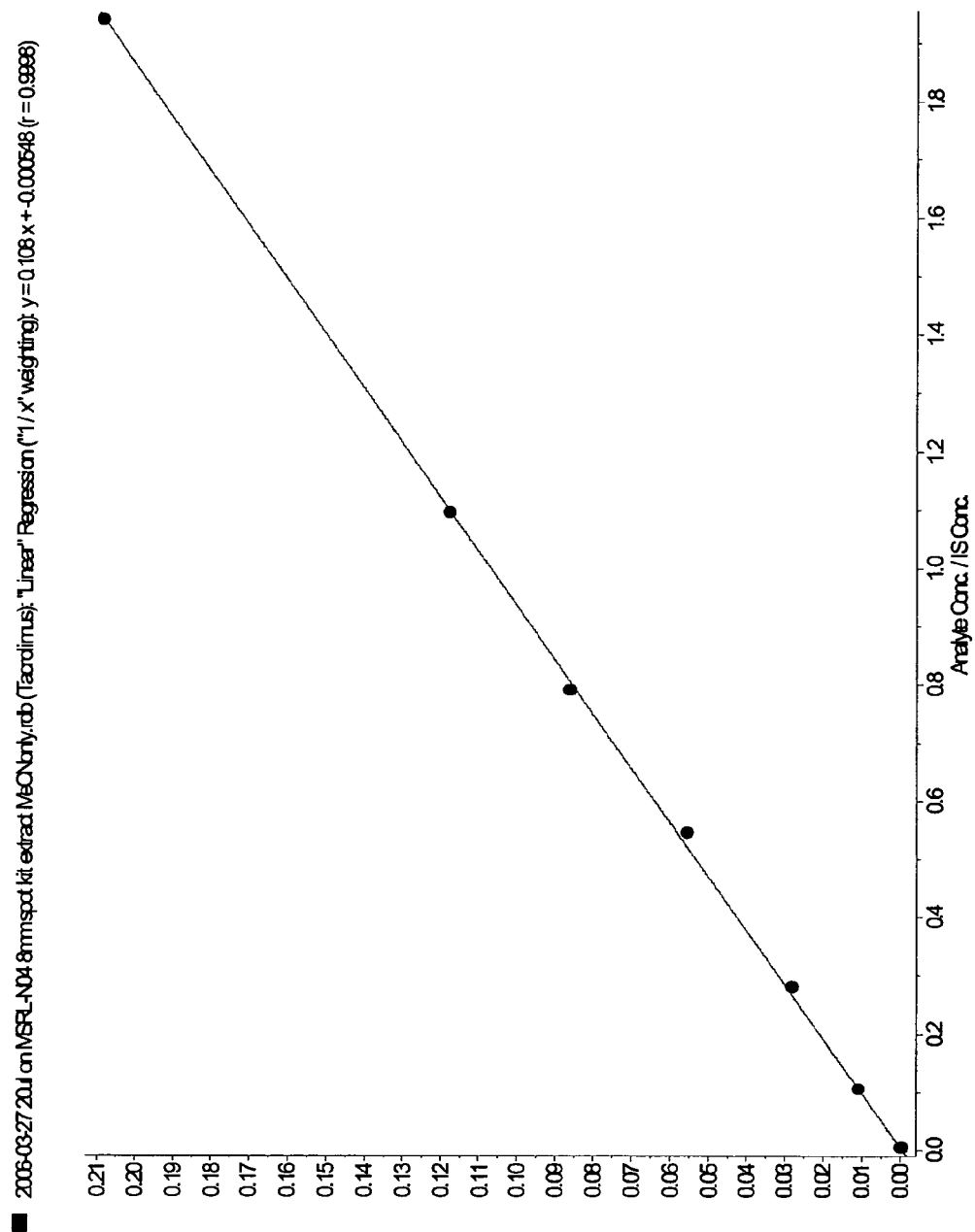
Figure 8. Tacrolimus calibration curve (r=0.9998)

DEVICE FOR QUANTITATIVE ANALYSIS OF A DRUG OR METABOLITE PROFILE

This application claims priority of U.S. application Nos. 60/694,983, and 60/694,984, each filed Jun. 30, 2005, the entire contents of which are hereby incorporated by reference.

BACKGROUND OF THE INVENTION

1. Field of the Invention

The invention relates to a device, in particular to a sample preparation device for the quantitative analysis of a drug and/or metabolite profile in a biological sample. Moreover, the invention relates to an insert for such a device, an internal standard, and to a kit containing the device. Furthermore, the invention also relates to an apparatus containing the device, and to a method for the quantitative analysis of a drug and/or metabolite profile in a biological sample employing the device.

2. Description of the Related Art

Metabolomics is generally defined as the analysis of a substance or group of substances necessary for or taking part in a particular metabolic process in a human or animal body. It's also known as the metabolome analysis. Metabolomics is an evolving discipline that studies unique chemical fingerprints reflecting metabolic changes related to disease onset and progression. Metabolite profiling, an area within metabolomics, measures small molecules or metabolites, contained in a human cell, tissue or organ, which are involved in primary and intermediary metabolism. The biochemical information resulting from metabolite analysis reveals functional endpoints associated with physiological and pathophysiological processes, influenced by both genetic predisposition and environmental factors, such as nutrition, exercise or medication (Harrigan, G. G. & Goodacre, R. (2003) Metabolic profiling: Its role in biomarker discovery and gene function analysis. Kluwer Academic Publishers, Boston/Dordrecht/London; Schmidt, C. (2004), *Journal of the National Cancer Institute*, 96, 732-734; Raudys, S. (2001) *Statistical and neural classifiers*, Springer-Verlag, London; Daviss, B. (2005) *The Scientist*, 19, 25-28). Metabolite profiling in combination with data mining approaches have the potential to revolutionize clinical diagnosis and drug development. In particular, big pharma companies are under continuous pressure to discover new targets and novel, more efficacious and safer compounds, and expedite biomarker and drug discovery, and generally lower costs of pharmaceutical development. Therefore they rely increasingly on biotech companies to fill this innovative gap and future pipelines. In this context, innovative bioanalytical and data mining techniques will play a fundamental role in saving costs by reducing time to market and drug attrition rates.

Recently, due to significant advances in high-throughput technologies, a wider set of the human metabolome—a thus far largely unexplored source of bioinformation—is now accessible (Beecher, C. (2003). In Harrigan, G. G., Goodacre, R. (Ed). *Metabolic profiling: Its role in biomarker discovery and gene function analysis* (pp. 311-319). Kluwer Academic Publishers, Boston/Dordrecht/London; Dunn, W. B., Bailey, N. J. & Johnson, H. E. (2005) *Analyst*, 130, 606-625). Statistical comparison of metabolite profiles can expose multivariate patterns that have the potential to revolutionize the health care system by specifically capturing latent warning signs of up-coming diseases before any disease symptoms show up. Early disease screening and prevention, opposed to late disease detection and expensive therapeutic interventions, is probably the primary solution to affordable health care coverage in the future. By definition, these so called biomarkers are "objectively measured indicators of normal biological processes, pathogenic processes or pharmacological responses to a therapeutic intervention, and intend to substitute for a clinical endpoint (predict benefit or harm) based on epidemiologic, therapeutic, pathophysiologic or other scientific evidence" (Biomarkers Definitions Working Group. (2001) *Clinical Pharmacology and Therapeutics*, 69, 89-95). Interest in the discovery of novel biomarkers originates from their broad range of potential applications and fundamental impact on pharmaceutical industry dynamics and current health care sector principles. Successful implementation of biomarkers in drug discovery can reduce the time and cost of drug development while the application to molecular diagnostics will improve patient compliance in clinical settings and reduce unnecessary costs resulting from false diagnosis in addition to late disease detection (Stoughton, R. B. & Friend, S. H. (2005), *Nature Reviews Drug Discovery*, 4, 345-350; Morris, M., & Watkins, S. M. (2005), *Current Opinion in Chemical Biology*, 9, 407-412; McCandless, S. E. (2004), *Primary Care*, 31, 583-604).

Qualitative and quantitative metabolite profiling technologies include a range of advanced analytical and data processing tools, with the objective of utilizing potential markers as a result of comparison of small molecule components of biological systems. Tandem mass spectrometry (MS), for example, detects hundreds of metabolites simultaneously from micro liter quantities of biological samples, such as whole blood, serum, plasma, urine or other body fluids from minute amounts, with high precision and sensitivity (Roschinger, W., Olgemoller, B., Fingerhut, R., Liebl, B. & Roscher, A. A. (2003), *European Journal of Pediatrics*, 162 (Suppl 1), S67-76; Strauss, A. W. (2004), J Clin Invest 2004; 113:354-356; Kaltashov, I. A. & Eyles, S. J. (2005), *Mass spectrometry in biophysics: Conformation and dynamics of biomolecules*, Wiley). Quantification is achieved by reference to a wide range of appropriate internal standards.

For example, WO 03/005628 describes a method for generating, viewing, interpreting and analyzing a quantitative database of metabolites. Further, U.S. Publication 2002/0009740 describes methods for drug discovery, disease treatment and diagnosis using metabolomics. U.S. Pat. No. 6,455,321 describes a method for interpreting tandem mass spectrometry data for clinical diagnosis. U.S. Pat. No. 6,258,605 describes an analytical method to screen the newborn populations' acylcarnitine and amino acids from blood samples. U.S. Pat. No. 6,627,444 describes a sampling device to aid in calibrating a field instrument.

Furthermore, U.S. Publication 2006/0057554 describes a sample collection device that includes a support bearing an inert absorbing matrix for a fluid sample, wherein the matrix preferably comprises pre-calibrated selected inorganic analytes as internal standards. Moreover, U.S. Publication 2003/0199102 describes a testing tray comprising multiple cells, wherein the cells contain a tried internal standard. The testing tray is for conducting multiple of tests on a biological fluid.

In order to handle the biological samples to be evaluated, further sample devices are known in the related art. For example, Tanaka et al., Clinical Chemistry 47:10, 1829-1835 (2001) describes a microvolume blood-sampling device with low hemolysis and high consistent yield of serum components.

However, the known sample devices show several disadvantages. In particular, the device described in U.S. Pat. No.

6,627,444 is designed for releasing calibration compounds by way of heating only. It is also designed solely for calibrating an instrument.

Other devices like the device disclosed in U.S. Publication 2006/0057554 fail to use identical organic compounds labelled with stable isotopes preimbedded in a specially designed device for extracting and derivatising.

As a result, there is a need to provide for an improved, highly efficient and reliable quantitative analysis of a drug profile or a metabolite profile in a biological sample, i.e., of concentrations of primarily endogenous, but not excluding exogenous compounds like drugs and metabolites thereof and metabolites from various biological samples.

SUMMARY OF THE INVENTION

In view of the problems of the related art discussed above, it is an object of the invention, in part, to provide for an improved quantitative analysis of a drug profile or a metabolite profile in a biological sample, i.e. of concentrations of primarily endogenous, but not excluding exogenous compounds like drugs and metabolites thereof and metabolites from various biological samples, being highly efficient and reliable. Moreover, an improved analysis is provided that is relatively salt free, which is important for mass spectrometry analysis.

The invention, in part, pertains to a sample preparation device that may be used for the quantitative analysis of a drug and/or metabolite profile in a biological sample. Moreover, it is also an object of the present invention to provide for an insert for such a device, a kit comprising the device and an apparatus containing the device.

In a first aspect the invention, in part, provides an insert for a device suitable for the quantitative analysis of a drug profile and/or a metabolite profile in a biological sample comprising (a) a support impregnated with (b) at least one internal standard.

In a second aspect the invention, in part, provides a device for the quantitative analysis of a drug and/or metabolite profile in a biological sample comprising (a) one or more wells or vials, and (b) an insert according to the first aspect of the invention.

In a third aspect the invention, in part, provides an internal standard for the quantitative analysis of a drug and/or metabolite profile in a biological sample being encapsulated and suitable for being employed according to the first aspect.

In a fourth aspect the invention, in part, provides a kit for the quantitative analysis of a drug and/or metabolite profile in a biological sample comprising the device according to the second aspect of the invention.

In a fifth aspect the invention, in part, provides an apparatus for the quantitative analysis of a drug and/or metabolite profile in a biological sample comprising (a) a treatment unit for preparing the drug and/or metabolite to be screened comprising (a1) an automated liquid handling system, and (a2) at least one device according to the second aspect of the invention for derivatisation of the drugs and/or metabolites present in the sample and for subsequent extraction of the derivatives; (b) a mass spectrometer for the quantitative targeted mass spectrometry-based analysis, and (c) database for storing results of the analysis.

In a sixth aspect the invention, in part, provides a method for the quantitative analysis of a drug and/or metabolite profile in a biological sample employing the insert and/or the device and/or the internal standard and/or the kit and/or the apparatus of the invention.

A further aspect of the invention, in part, pertains to a device that includes a support formed from a sorbent material and multile mass spectrometry, organic, metabolite standards of known amounts impregnated in the support and dried. The mass spectrometry, organic, metabolite standards can be amino acids labelled with stable isotopes, can be polypeptides labelled with stable isotopes, can be lipids labelled with stable isotopes, or can be acylcarnitines labelled with stable isotopes. The device can also include a well and a retainer, wherein the retainer holds the support within the well. The invention, in part, pertains to a device that includes a support formed from a sorbent material; and multiple mass spectrometry, immunosuppressant drug standards of known amounts impregnated in the support and dried, and the immunosuppressant drug standards can be one or more of Everolimus and Cyclosporin D. The device can also include a well and a retainer, wherein the retainer holds the support within the well.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

FIG. 2 describes a neutral loss scan of 135 in negative mode using ion tandem mass spectrometry of phenylthiourea amino acid derivatives (PTU), showing amino acids from a red blood cell sample and their corresponding stable isotope internal standards prepared with the multi-device described in Example 2.

FIG. 3A describes a precursor scan 184 in positive ion mode (A), showing the multi-devices ability to extract phospholipids from a red blood cell sample of Example 2. For example sphingomyelins and phosphatidylcholines are observable in the m/z range of about 700-840, and lyso phosphatidylcholines in the m/z range of about 400-650.

FIG. 3B describes an MRM scan (multiple reaction monitoring) in positive ion mode of Example 2.

FIGS. 4A-4C describe examples of how immunotherapy drugs Sirolimus, Everolimus, Cyclosporin A, Tacrolimus, and internal standards Ascomycin and Cyclosporin D from a quality control blood sample are analysed with LCMS to generate quantitative data. The area under the integrated peaks of the internal standard Cyclosporin D and Ascomycin, of known concentrations, are used for comparison against the area under the peak of the immunosuppressants in the five quality control samples containing known concentration amounts. This provides a measure of accuracy for all four drugs.

FIG. 5 describes a calibrator curve from calibrators for Sirolimus obtained from multi-device with cellulose insert (Example 3).

FIG. 6 describes a calibrator curve from calibrators for Everolimus obtained from multi-device with cellulose insert (Example 3).

FIG. 7 describes a calibrator curve from calibrators for Cyclosporin A obtained from multi-device with cellulose insert (Example 3).

FIG. 8 describes a calibrator curve from calibrators for Tacrolimus obtained from multi-device with cellulose insert (Example 3).

DETAILED DESCRIPTION

Figure 1:
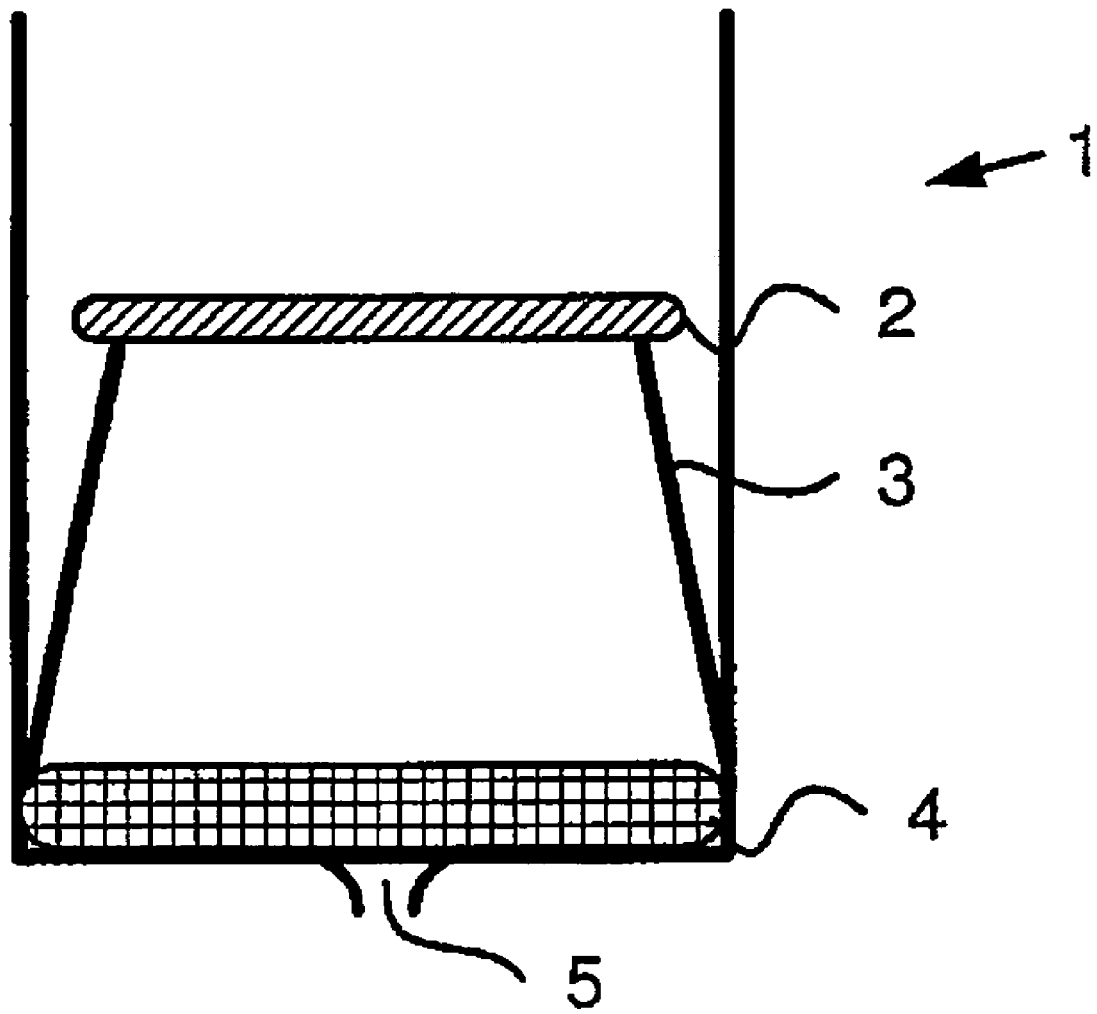
FIG. 1 describes a cross-sectional view of a singular device according to the invention containing wells or vials and its assemblage from individual components. Reference number (1) shows a well/vial. Reference number (2) shows an insert according to the invention that contains an immobilising stationary phase of glass, celluloses or other suitable material (i.e. a porous support) containing internal standards with optional (micro)encapsulation; reference number (3) shows a retainer to hold the porous support in the well or vial, which is chemically inert to derivatives and solvent; reference number (4) shows a filter; reference number (5) shows an outlet, which opens under pressure of centrifugal or gravitational force or vacuum.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention will be described in more detail hereinbelow by making reference to its particularly preferred embodiments.

The invention, in part, pertains to a simple device containing pre-measured internal standards (reference compounds in general) in a vial or well, to which biological samples to be measured can be added for further treatment and eventual analysis by e.g. mass spectrometry. The device includes an insert that can be porous and contains one or more internal standards of known molar amounts. Additionally, these internal standards may also be encapsulated and/or embedded into a protective matrix to prolong shelf-life. The protective matrix includes, but is not limited to, either a non-naturally occuring phosphatidylcholine, a polyethylene glycol polymer, a viscous glycerol or sorbitol solution. The device can be used for analyzing a metabolite profile and/or for analyzing a drug profile (i.e. therapeutic drug monitoring, TDM) in a biological sample. Thus, it should be understood that even if the invention will be described in the following for the analysis of a metabolite profile, it is not limited thereto. In contrast, the same considerations also apply for the analysis of a drug profile.

Below, the components of the device according to the invention as well as the utilization of the device will be explained.

The device according to the invention contains (A) one or more wells/vials, and (B) at least one insert. The insert is formed from (a) a porous support which is (b) impregnated with at least one internal standard. The insert is indicated as reference number (2) in FIG. 1.

Insert

The term "insert" as used in the invention should be understood to be the support containing the internal standards with an optional chemical protectant. The insert may have any geometrical form as long as the insert fits into the well or vial of the device. In a preferred embodiment, the insert is arranged within the well or vial of the device by using a retainer. The retainer is indicated as reference number (3) in FIG. 1. In a particularly preferable embodiment of the invention, the retainer (3) allows the insert to be arranged within the well without any direct contact between the insert and the well. Thus, the insert (2) is located above the bottom of the well (1) preferably within a distance of about 2 to 10 mm, more preferably of about 3 to 5 mm by using the retainer (3). In other words, in a preferred embodiment there is a so-called "gap" or "distance" between the bottom of the well (1) and the insert (2) and/or between the walls of the well (1) and the insert (2). As the retainer (3), any retainer is suitable as long as it allows the formation of the gap between the bottom of the well (1) and the insert (2). Such an arrangment allows for maximum surface area of the support to precipitate the samples onto. The design further ensures the insert (2) is fully accessed by flow of air or other drying gas around the insert (2) to enable rapid drying of sample after application. This design principal also ensures the insert (2) is fully accessed by flow of solvent from all sides enabling metabolite or drug extraction from sample with minimized protein or salt contaminants. Thus, the pores of the support allow a reaction (derivatisation) to proceed within the support itself, minimizing solvent usage and also subsequent removal as evaporation of excess derivative and solvents is provided by maximum surface area to circulating drying gases (air or nitrogen) around the sample. The increased surface area and solvent mobility around the entire support also ensures high extraction efficiencies using appropriate solvents. In other words, the above-mentioned gap allows an almost free arrangement of the insert within the well (1) and an improved circulation of fluids flowing through the well (1).

Moreover, according to one preferred embodiment of the invention, the device may include more than one insert arranged in stacks, wherein the respective inserts are more preferably arranged with the above-mentioned gap between each other in order to allow the circulation of fluids.

Support

The support as used in the invention may be any support preferably with at least medium degree, preferably a high degree of porosity. Such a support in principle is known in the related art and also commercially available.

The porosity Φ of a medium (i.e. the support) is defined to be the proportion of the non-solid volume to the total volume of material, and is defined by the ratio:

$$\Phi = V_p/V_m$$

In the ratio, $V_p$ the non-solid volume (pores and liquid) and $V_m$ is the total volume of material, including the solid and non-solid parts.

Thus, porosity has a value between 0 and 1, typically ranging from less than 0.01 for solid granite to more than 0.5 for peat and clay, although it may also be represented in percent terms by multiplying the fraction by 100%. The porous support of the invention has a porosity of at least about 30%, more preferably at least about 50%, even more preferably at least about 70%, and most preferably at least about 90%.

The porous support as used in the insert may be of any suitable material, but it is preferably a solid support. More preferably, the porous support is formed from a sorbent material for liquids (also named liquid sorbent material). Still more preferably, the support is consisting of the liquid sorbent material. The sorbent material may be an adsorbent or an absorbent material.

A liquid sorbent material as used in the invention should be understood to be any material that allows solutions of internal standards and subsequent samples for analysis to be adsorbed or absorbed uniformly throughout the pores additionally allowing carrier solvent removal by evaporation.

The liquid allowed to being ad- or absorbed by the support material can be any kind of liquid, but it is preferably a volatile liquid at atmospheric pressure, for example a liquid having a boiling point less than about 250 degrees Centigrade (C) at atmospheric pressure.

More preferably, the liquid sorbent material according to the invention is formed from at least one of a carbohydrate material, such as cellulose material, glass fibres, glass beads, polyacrylamide gel, porous plastic inert polymer and porous graphite. The porous sorbent material may more preferably be formed from a carbohydrate material or derivative thereof, such as agarose, agar, cellulose, dextran, chitosan, konjac, carrageenan, gellan, or alginate. The liquid sorbent material is, however, most preferably made of cellulose or glass fibers. The shape of the support or liquid sorbent material is not particularly limited but preferably is of a circular, square or scroll or nautilus dimension. According to the invention, the shape of the support or sorbent material is adapted to the shape of the well or vial of the device. As mentioned, the porous support or sorbent material may be fixed or secured in its position in the well or vial (1) by a fixing structure such as a retainer (indicated as (3) in FIG. 1).

The porous support formed from the liquid sorbent material mainly has two functions. The first is to embed the internal standards (reference material) as descibed below at predefined concentration ready for addition of the biological sample. The second is the immobilizing of the contents of each sample. This immobilizing step induces cell lysis, protein immobilization/precipitation and salt and many other drug or metabolite retention from each of the samples. The porosity of the support is then essential for maximal exposure to both the derivatizing agents and also the extraction solvent to be added for the analysis.

Internal standard

An internal standard as used in the invention should be understood to be any reference materials of known absolute amounts that are used for comparisons to similar or identical compounds in order to quantify unknown amounts of compounds present in a given sample. Preferably, the internal standard is an organic internal standard. Internal standards as used in the present invention may belong to the same group or family of compounds to be analyzed in the biological sample. However, they are preferably labelled with isotopes in order to properly allow a distinction between the metabolites of the sample and the internal standard. Any other way of distinguishing the metabolites of the sample from the internal standards, however, may also be used. For example, non-naturally occuring compounds may also be used as internal standards.

Specific examples for the internal standard as are preferably used in the present invention are listed in Table 1 below.

TABLE 1

Lipids:

| abbreviation | Full name | Comments Fatty acid chain length |
|---|---|---|
| SM(d18:1/6:0) | N-Hexanoyl-sphing-4-enine-1-phosphocholine | 6 |
| GPCho(9:0/0:0) | 1-Nonanoyl-sn-glycero-3-phosphocholine | 9 |
| GPCho(14:0/14:0) | 1,2-Ditetradecanoyl-sn-glycero-3-phosphocholine | 28 |
| GPIns(16:0/16:0) | 1,2-Dihexadecanoyl-sn-glycero-3-phospho-(1'-myo-inositol) | 32 |
| GPCho(20:0/20:0) | 1,2-Di-(3,7,11,15 tetramethyl hexadecanoyl)-sn-glycero-3-phosphocholine | 40 |
| GPSer(20:0/20:0) | 1,2-Di-(3,7,11,15 tetramethyl hexadecanoyl)-sn-glycero-3-phosphoserine | 40 |
| GPSer(6:0/6:0) | 1,2-Dihexanoyl-sn-glycero-3-phosphoserine | 12 |

| Abbreviation | Full name | Comments |
|---|---|---|
| 13C2-15N-Gly | 13C2-15N-Glycine | |
| D4-DL-Ala | D4-DL-Alanine | |
| 15N2-L-Argl | 15N2-L-Arginine HCl | |
| D3-DL-Asp | D3-DL-Aspartic Acid | |
| 15N2-L-Asn | 15N2-L-Asparagine H2O | |
| D3-L-Glu | D3-L-Glutamic Acid | |
| D5-L-Gln | D5-L-Glutamine | |
| 13C6-L-His | 13C6-L-Histidine H2O | |
| 13C6-L-Ile | 13C6-L-Isoleucine | |
| 13C-L-Lys | 13C-L-Lysine 2HCl | |
| D3-L-Met | D3-L-Methionine | |
| D6-L-Orn | D6-L-Ornithine HCl | |
| D5-L-Phe | D5-L-Phenylalanine (ring 5-phe) | |
| D7-L-Pro | D7-L-Proline | |
| D3-DL-Se | D3-DL-Serine | |
| 13C4-L-Thr | 13C4-L-Threonine | |
| 15N2-L-Trp | 15N2-L-Tryptophan | |
| D4-L-Tyr | D4-L-Tyrosine (ring 4-tyr) | |
| D8-DL-Val | D8-DL-Valine | |

Acylcarnitines

| Abbreviation | Full name | side chain length |
|---|---|---|
| D3-C0 | [d3-methyl]-Carnitine.HCl | C = 0 |
| D9-C0 | [d9-trimethyl]-Carnitine.HCl | C = 0 |
| D3-C2 | [d3]-Acetyl-L-carnitine.HCl | C = 2 |
| D3-C3 | [3,3,3-d3]-Propionyl-L-carnitine.HCl | C = 3 |
| D3-C4 | [4,4,4-d3]-Butyryl-L-carnitine.HCl | C = 3 |
| D7-C4 | [d7]-Isobutyryl-L-carnitine.HCL | C = 4 |
| D3-C5 | [5,5,5,-d3]-Valeryl-L-carnitine.HCl | C = 4 |
| D9-C5 | [d9]-Isovaleryl-L-carnitine.HCl | C = 5 |
| D3-C6 | [6,6,6-d3]-Hexanoyl-L-carnitine.HCl | C = 6 |
| D3-C8 | [8,8,8-d3]-Octanoyl-L-carnitine.HCl | C = 8 |
| D3-C10 | [10,10,10-d3]-Decanoyl-L-carnitine.HCl | C = 10 |
| D3-C12 | [12,12,12-d3]-Dodecanoyl-L-carnitine.HCl | C = 12 |
| D3-C14 | [14,14,14-d3]-Tetradecanoyl-L-carnitine.HCl | C = 14 |
| D3-C16 | [16,16,16-d3]-Hexadecanoyl-L-carnitine.HCl | C = 16 |
| D3-C18 | [18,18,18-d3]-Octadecanoyl-L-carnitine.HCl | C = 18 |

Reducing Monosaccharides

| Abbreviation | Full name | Comments |
|---|---|---|
| 13C6-Glc | 13C6-Glucose | |

Pyruvate/Lactate

| Abbreviation | Full name | Comments |
|---|---|---|
| 13C3-Pyr | 13C3-Pyruvate | |

Creatinine

| Abbreviation | Full name | Comments |
|---|---|---|
| | [d3-methyl]-Creatinine | |

Immunosuppressants

| Abbreviation | Full name(s) | Comments |
|---|---|---|
| | Ascomycin | |
| | Cyclosporin D | |
| | 32-Desmethoxyrapamycin | |

Biological Sample

A biological sample as used in the invention should be understood to be any sample of, relating to, caused by, or affecting life or living organisms, biological processes, such as growth and digestion.

Examples of a biological sample may include, but are not limited to blood, cell culture supernatant, saliva, tears, urine, blood serum, plasma, sweat, vaginal fluids, semen, feces, mucous, breast milk, ascites, lymph, pleural effusion, synovial fluid, bone marrow, cerebro-spinal fluid, and washings from bodily cavities (e.g., bronchial lavage), hair, tissue, bones, or teeth.

Preferably, the biological sample is a liquid sample. More preferably, the biological sample is blood, and most preferable human blood. Liquid means a state of matter with definite volume but no definite shape at 25° C., like water.

Metabolite Profile

A metabolite profile as used in the invention should be understood to be any defined set of values of quantitative results for metabolites that can be used for comparison to reference values or profiles derived from another sample or a group of sampels. For instance, a metabolite profile of a sample from a diseased patient might be significantly different from a metabolite profile of a sample from a similarly matched healthy patient.

Metabolites, such as, but not limited to, amino acids, peptides, acylcarnitines, monosaccharides, lipids and phospholipids, prostaglandins, hydroxyeicosatetraenoic acids, hydroxyoctadecadienoic acids, steroids, bile acids and glyco- and phospholipids can be detected and/or quantified.

Examples of metabolites that are amenable to mass spectrometic analyses according to the invention are listed in Table 2. In particular, lipid species from C4:X to C46:X (where X, the degree of saturation, ranges from 0 to 8) in any given fatty acid residue are shown. The lipids include also sphingolipids and glycosphingolipids.

Amino acids, which can be detected and quantified, are proteogenic or non-proteogenic amino acids. The proteogenic amino acids and the non-proteogenic amino acids, as indicated in Table 2, are preferred.

Acylcarnitines from C4:X to C18:X (wherein X is the degree of saturation and ranges from 0 to 8 in any given acid residue) can be detected and/or analyzed. Examples for acylcarnitines which are preferred are also listed in Table 2.

TABLE 2

| | Lipids: | |
|---|---|---|
| abbreviation | Full name of lipid subtype Glycerophospholipids, sphingoliplds and glycosphingolipids | Comments Fatty acid chain length |
| Sph | sphingosine | None |
| Cer | ceramide | C6:X–C36:X |
| SM | sphingomyelin | C6:X–C36:X |
| Sph pchol | sphingosylphosphorylcholin | None |
| Sph dh | dihydrosphingosine | None |
| PC | phoshatidylcholine | C4:X–C46:X |
| PI | phosphatidylinositol | C4:X–C46:X |
| PS | phosphatidylserine | C4:X–C46:X |
| PC (a) | lysophoshatidylcholine | C4:X–C32:X |
| PI (a) | lysophosphatidylinositol | C4:X–C32:X |
| PS (a) | lysophosphatidylserine | C4:X–C32:X |
| PC (e) | plasmenylphoshatidylcholine | C4:1–C32:X |
| PC (e) | plasmanylphoshatidylcholine | C4:0–C32:0 |

Amino Acids
Proteinogenic Amino Acids

| | abbreviation | Full name | Comments |
|---|---|---|---|
| A | Ala | Alanine | |
| D | Asp | Aspartic acid | |
| E | Glu | Glutamic acid | |
| F | Phe | Phenylalanine | |
| G | Gly | Glycine | |
| H | His | Histidine | |
| | Xle | Leucine/Isoleucine | |
| K | Lys | Lysine | |
| M | Met | Methionine | |
| P | Pro | Proline | |
| R | Arg | Arginine | |
| S | Ser | Serine | |
| T | Thr | Threonine | |
| V | Val | Valine | |
| W | Trp | Tryptophan | |
| Y | Tyr | Tyrosine | |
| | ADMA | Asymmetrical dimethyl arginine | LC MS method |
| | SDMA | Symmetrical dimethyl arginine | LC MS method |
| Q | Gln | Glutamine | |
| N | Asn | Asparagine | |
| | | Nitrotyrosine | LC MS method |
| | | Hydroxyproline | LC MS method |
| | | Kynurenine | LC MS method |
| | | 3-Hydroxy kynurenine | LC MS method |

Non-Proteinogenic Amino Acids

| | abbreviation | Full name | Comments |
|---|---|---|---|
| O | Orn | Ornithine | |
| | Cit | Citrulline | |

Acylcarnitines

| abbreviation | Full name | Comments |
|---|---|---|
| C0 | Carnitine (free carnitine) | C0 |
| C2:X to C18:X | Acylcarnitine | C0:X to C26:X |
| C3:X-OH to C18:2-OH | Hydroxylacylcarnitine | C3-OH to C18:2-OH |
| C3:0-DC to C18:2-DC | Dicarboxylacylcarnitines | C3:0-DC to C12:0-DC |

Reducing Monosaccharides

| abbreviation | Full name(s) | Comments |
|---|---|---|
| H | Hexose | |
| P | Pentose | |
| dH | Deoxyhexose | |

Others

| abbreviation | Full name | Comments |
|---|---|---|
| Cr | Creatinine | |
| | Spermidine | LC MS method |
| | Spermine | LC MS method |
| | Putrescine | LC MS method |
| | Dopamine | LC MS method |
| | Serotonin | LC MS method |
| | Prostaglandins | LC MS method |
| | Hydoxyeicosatetraeneoic (HETEs) | LC MS method |
| | Hydroxyoctadecadienoic (HODEs) | LC MS method |
| | Leukatrienes | LC MS method |
| | Thromboxanes | LC MS method |
| | Bile acids | LC MS method |
| | Sterols | LC MS method |
| | Cholesterols | LC MS method |
| | Vitamins and cofactors | |
| | Drugs and drug metabolites | LC MS method |

Drug Profile

A drug profile as used in the invention should be understood to be any defined set of values of quantitative results for one or more drugs or drug metabolites in a specified sample. Moreover, immunosuppressants as specific examples can also be detected and quantified. For example, a drug profile of a transplant patient would give the physician the immediate circulating amounts of one or more drug therapies in use, and future dosages could therefore be increased or decreased according to the quantities measured to achieve best therapeutic range. Such an analysis is designated as therapeutic drug monitoring (TDM). Immunosuppressants in accordance with the present invention are to be understood as drugs that may be used in immunosuppressive therapy to inhibit or prevent activity of the immune system. Clinically they are used to prevent the rejection of transplanted organs and tissues and in treatment of autoimmune diseases such as rheumatoid arthritis, myasthenia gravis, systemic lupus erythematosus, Crohn's desease, and ulcerative colitis. Immunosupperessants as defined herein basically can be classified into four groups: glucocorticoids, cytostatics, antibodies, and drugs acting on immunophilins. Preferred examples of immunosuppressants as used in the present invention are Cyclosporin A, Sirolimus, Everolimus and Tacrolimus.

Encapsulation of the Standards

The internal standard according to the invention can be, but does not have to be encapsulated with a covering material or protecting material protecting the internal standard from degradation and chemical reactivity prior to use. The protection of the internal standard from degradation and chemical reactivity can prevent many forms of breakdown or chemical modification of the internal standard, such as prevention of the action of sunlight, temperature, and microorganisms, in particular prevention from any process that transforms the internal standard into breakdown or degradation products, thereby influencing the outcome of a quantitative analysis.

A protecting/covering material as used in the invention should be understood to be any material for shielding or designed to shield the internal standard(s) against degradation.

The protecting/covering material according to the invention can be any material suitable for protecting the internal standard from an environmental influence as mentioned above. The covering material according to the invention preferably comprises at least one of a polymer, a micelle-forming compound, a liposome-forming compound and a polyhydroxy compound, or any mixtures thereof.

If the covering material is a polymer, the polymer is not particularly limited and may be a high molecular weight organic compound, such as one having a weight average molecular weight of at least about 500 g/mol, at least about 1,000 g/mol, at least about 5,000 g/mol or at least about 10,000 g/mol, which is either natural or synthetic, whose structure can be represented by a repeated small unit of a monomer. A synthetic polymer is formed in a manner known in the art such as by addition or condensation polymerization reaction of monomers. The polymer of the invention may also be a co-polymer, when two or more different monomers are involved. A homopolymer is a polymer that is formed from only one type of monomer.

The polymer according to the invention is preferably a polyalkylene glycol homopolymer or copolymer or a mixture thereof. The weight average molecular weight is preferably about 1000 daltons (Da). More preferably the polymer according to the invention is a polyethylene glycol (PEG) or polypropylene glycol (PPG), preferably PEG 1000 having a weight average molecular weight of about 1000 Da, as it is soluble or miscible with highly polar and less polar to unpolar solvents.

If the covering material is a micelle-forming compound, the compound used in the invention should be understood to be any compound that can induce submicroscopic aggregation of molecules, such as droplets in a colloidal system. The micelle-forming compound according to the invention is preferably a surfactant.

A surfactant as used in the invention is understood to be any chemical compound that reduces the surface tension between two liquids; or any surface-active agent which increases the emulsifying, foaming, dispersing, spreading and wetting properties of a product, in particular any organic compound whose molecules contain a hydrophilic group at one end and a lipophilic group at the other end. Suitable surfactants comprise cationic, anionic, nonionic, and amphoteric surfactants. Preferably, the surfactant can be phosphatidyl $(C17:O)_2$.

If the covering material is a liposome-forming compound said compound as used in the invention should be understood to be any compound which can build artificial microscopic vesicles formed from an aqueous core enclosed in one or more phospholipid layers, used to convey vaccines, drugs, enzymes, or other substances to target cells or organs.

A phospholipid as used in the invention is understood in the general way in the art and may be a phosphorous containing lipid, such as lecithin and cephalin, made of glycerol and fatty acids, with a phosphate group attached. More preferably, the liposome forming compound is a phospholipid, such as a phosphatidyl choline or a phosphatidyl ethanolamine or derivatives thereof.

If the covering material is a polyhydroxy compound said compound as used in the invention should be understood to comprise at least two hydroxy groups. Most preferably the polyhydroxy compound is sorbitol and/or glycerol.

Preferably, the encapsulation according to the invention is microencapsulation. Microencapsulation as used in the invention should be understood to be any encapsulation of microcapsules, which are small, preferably microscopic capsules designed to release their contents when broken by pressure, dissolved or melted. In particular, the capsules of the invention preferably have a diameter of less than about 100 micrometer, more preferably less than about 10 micrometer and most preferably less than 1 about micrometer.

Microencapsulated internal standards are robust in terms of storage and shipping and are stable regarding oxidation and degradation processes, and they have a relatively long shelf-life. The microencapsulation is preferably standardized to prepare synthetic quality control material based on microencapsulated components. This is typically achieved by drying internal standards and other protected samples down with the covering material in a solvent that is a suitable solvent for these compounds like a chloroform/methanol mixture for phospholipids. Typically addition of water to these samples induces micelle and/or liposome formations to occur, and embedding of these internal or external standard lipophilic protected compounds is then made possible in water.

For example, the device may be prepared as follows: The internal standard, dissolved in a suitable solvent, is pipetted in a known amount onto a porous support and dried. This procedure is repeated for every internal standard or class of internal standards to be employed in the device. If an encapsulation is provided, as the final step, the encapsulating/covering material, preferably in a suitable solvent, is put onto the support including the internal standards (i.e. the insert) and dried. The insert is then inserted into the well, preferably by using a securing means or fixing structure such as a retainer. As an alternative, the support may be inserted into the well before pipetting the internal standards and the optional covering material onto the support.

Multiple Devices

A multi-device as used in the invention should be understood to be any multiple devices joined together to form a multi-device such as a microtiter plate standard format.

A microtiter plate as used in the invention should be understood to be any plastic sample holder used in biology or chemistry research facilities. The microtiter plate standard was formalized by the Society for Biomolecular Screening (SBS) in 1996. It typically has 6, 24, 96, 384 or 1536 sample wells arranged in a 2:3 rectangular matrix. The standard governs well dimensions (e.g. diameter, spacing and depth) as well as plate properties (e.g. dimensions and rigidity).

For the multi-device, the same description of constituting components as mentioned above applies. Therefore, also the multi-device includes a porous support such as cellulose or glass fibre as examples, preferably retained in at least one well by a chemically inert retaining structure. The porous support has embedded into it internal standards in a dry state; optionally microencapsulated (coated) with a protective or covering material or mixture of chemicals, for example polyethylene glycol 1000, phosphatidylcholine, glycerol or sorbitol.

The device in multiple format herein named a multi-device may also have a different format. Pre-embedding several vials, for example 6 wells, yields a 6 point calibration with multiple calibrating compounds. Quality control samples containing known metabolites and/or multiple drug concentrations are also pre-embedded.

Well

A well as used in the invention should be understood to be any vial or tube consisting of a material, which is preferably solvent and derivative resistant, wherein an extraction or chemical reaction can take place.

The one or more wells (indicated as reference number (1) in FIG. 1) of the device preferably comprise at least one filter (indicated as (4) in FIG. 1) for separating micron size solids, more preferably exactly one filter (4) for separating micron size solids. The one or more wells of the device preferably comprise at least one outlet (5) in FIG. 1 for discharging the filtrate.

A filter contained in the well as used in the invention should be understood to be any porous material a liquid or gas is passed through in order to separate the fluid from suspended particulate matter. The filter (4) has preferably a pore size of about 50 to 0.01 micrometer, more preferably about 5 to 0.1 micrometer, and even more preferably about 1 to 0.3 micrometer. Most preferably, the filter (4) has a pore size of about 0.45 micrometer.

In the inventin, the filter (4) is preferably located between the insert (2) and the outlet (5).

Moreover, the outlet (5) according to the invention preferably opens under applied centrifugal force or reduced pressure, preferably below 500 mbar. The reduced pressure is preferably applied on the side of the outlet (5) of the well (1). Alternatively, an increased pressure on the side of the insert (2) can be applied in order to ensure a flow from the insert (2) to the outlet (5). Kit The device according to the invention may be further used in a kit for the quantitative analysis of a drug and/or metabolite profile in a biological sample. A kit as used in the invention may be understood to be any system of reagents, solvents, software inclusive of the device allowing preparation of metabolites for quantitative targeted analysis of a range of metabolites usually in conjuction with an analytical instrument.

Apparatus

The device according to the invention may also be used in an apparatus for the quantitative analysis of a drug and/or metabolite profile in a biological sample. Said apparatus comprises (a) a treatment unit for preparing the drug and/or metabolite to be screened comprising (a1) an automated liquid handling system, and (a2) at least one device as defined above for derivatisation of the drugs and/or metabolites present in the sample and for subsequent extraction of the derivatives; (b) a mass spectrometer for the quantitative targeted mass spectrometry-based analysis, and (c) database for storing results of the analysis.

The apparatus (or platform) as used in the invention should be understood to be any apparatus that allows the complete preparation of a biological sample ready for analysis by mass spectrometry. This encompasses processes of extraction, derivatization, desalting and concentrating. This also includes all possible combinations of some or all of these processes in a fully automated method, preferably incorporating a liquid handling system in combination with a sample centrifugal device, a sample heating and cooling device, a sample shaking device, a sample drying device, a sample pipetting device and a sample homogenization device.

A liquid handling system as used in the invention may be any mechanical device that allows accurate aspiration and dispensing of many types of solvents in and out of vials and microtitre plates. A liquid handling system may be operated via a computer and software in such a liquid handling system.

A database or data bank as used in the invention may be any collection of data arranged for ease and speed of search and retrieval.

A targeted mass spectrometry analysis as used in the invention may be mass spectrometry analysis, wherein one or more preset ion pairs are used, specifically defining and representing a known metabolite by a known fragmentation pattern that is characteristic for the corresponding analyte, for identification of the targeted metabolite. The obtained ion intensities are used together with the appropriate internal standard to calculate the concentration of the targeted metabolite. The internal standard is identified by using a characteristic ion pair (or several), their obtained ion intensities are related to the known concentration of the internal standard allowing the quantification of a corresponding targeted metabolite. The set of targeted metabolites is known in advance and can be pre-annotated. Therefore, detected and quantified metabolites are already annotated allowing a fast and direct interpretation. A tandem mass spectrometer is particularly preferred as a mass spectrometer capable of MSMS analyses to distinguish more specifically ion species. Preferably, the apparatus allows for automated standardized sample preparation and high-resolution tandem mass analytics procedures. In particular, the automated sample preparation procedure increases day to day reproducibility of reliable results and lower coefficients of variance (CVs). When, for example, analyzing a derivatized sugar with a precursor ion scan, the derivative itself can be detected by the mass spectrometer. In positive ion mode this is preferably the formation of the phenylmethylpyrazolone (PMP) (MH)+ ion at m/z 175. The composition of the carbohydrate itself or discret isomers are detectable.

When carrying out a metabolome analysis using the device according to the invention a quantity of hundreds of metabolites can be analysed simultaneously from microtiter quantities of biological material with high speed, precision and sensitivity using pre-analytical steps. Quality assured (QA) data is generated from individual samples in the matter of minutes and interpreted employing statistical software tools. This method also overcomes hitherto to existing analytical bottlenecks through pre-analytical standardization and automation, and user-friendly statistical and biochemical data interpretation. This integration of all components in the method of the invention into a new technology platform will make "biochemical fingerprinting" accessible for widespread application and will expedite the spread of metabolomics.

EXAMPLES

The invention will be further illustrated by the following non-limiting examples.

Preparation and Conditions of the Multi-Device

One multi-device was prepared using 7 mm cellulose spots (cut from generic card-10 539 859, Schleicher Schuell Biosciences GmbH, Dassel, Germany) as the porous support in each of the 96 wells of a Solvinert microtiter plate (MSRP N04, Millipore Corp. Mass., USA). These were fixed into place with manufactured retainers made from polypropylene (Biocrates, Tirol, Austria).

To analyze a selected subset of metabolites, in this case, amino acids, acylcarnitines and phospholipids from a sample, a selection of suitable internal standards of amino acids, acylcarnitines and lipids labelled with stable isotopes to represent all the twenty proteogenic phosphatidylcholines, sphingomyelins, and lyso species of each were used. These were pre-imbedded into the porous support of the multi-device by pipetting known amounts of each internal standard class, allowing each to dry within the porous support before adding the next mixture of internal standards, allowing to dry and so forth. In this example, there were added acylcarnitines followed by amino acids and last, a mixture of phospholipid internal standards in a water solution containing 0.1% w/w polyethyleneglycol 1000 (PEG 1000), a compound which served dual purposes. As a surfactant, PEG 1000 resides in the pores of the porous support coating all internal standards offering a protective barrier to otherwise degradative actions of exposure to oxygen and water.

When completely dry the multi-device technical validation samples were then added to the first five wells of the multi-device.

Well 1: a blank,
Wells 2 and 3: control mixtures of unlabelled metabolites,
Well 4: a quality control with low concentration metabolites (normal levels or 1 times), and
Well 5: a quality control with high concentration metabolites (levels 10 times normal).

The multi-device containing pre-embedded internal standards with additional control samples in wells 1 to 5 is then stored ready to use at 4° C.

Method of Using the Multi-Device

Example 1

For examplary purposes only, the following is a description of how the device as specified above is used to process samples for analysis of a selection of metabolites.

To analyze a subset of metabolites, amino acids, acylcarnitines and phospholipids from a sample, a selection of suitable internal standards of amino acids, acylcarnitines and lipids, stable isotope labelled to represent all the twenty proteogenic amino acids, the most abundant acylcarnitines and phospholipids including phosphatidylcholines, sphingomyelins, and lyso species of each were used. Upon addition of a predefined amount of sample, typically 10 µl of plasma, the internal standards and amino acids of the sample are mixed within the confines of the pores of the insert. Any subsequent treatment that causes loss or degradation of metabolites will therefore be correlated for by the internal standard. Derivatisation of the amino acids can then take place within the confines of the pores of the insert. The derivatizing reagent in this example consists of 15 µl of a 5% phenylisothiocyante in a 1:1:1 solution of pyridine, water, ethanol. This derivatisation process occurs at room temperature in less than 20 minutes. As the derivatising solution is completely volatile it can be simply removed under a gentle stream of nitrogen or vacuum at room temperature. The addition of a methanol solution containing 10 mM ammonium acetate extracts the derivatised amino acids, acylcarnitines and the phospholipids simultaeously from the porous device into the methanol solvent. The microtiter plate of choice for this purpose has additional properties. It has a 0.45 micron filter and a liquid outlet, that only opens under centrifugal force or vacuum, built into the bottom of each well. The methanol extract from the sample is then simply collected via centrifugation into a capture-microtiter plate, placed under the microtitre plate containing device. Mass spectrometry analysis of the solution from each well can then take place, typically using an autosampling instrument to deliver the sample to the mass spectrometer.

Example 2

The following will demonstrate that the device can be used to process samples for analysis of a selection of metabolites.

The multi-device upon accurate addition of 10 µl of blood samples from one patient to each well is mixed with the internal standards within the confines of the pores of the porous support (insert). Any subsequent treatment that causes loss or degradation of metabolites will therefore be correlated to the internal standard. Derivatization was carried out as in Example 1 and the resulting solutions from each well are then analyzed by mass spectrometry methods, typically using an autosampling instrument to deliver the sample to the spectrometer.

Results from the mass spectrometric measurements of the metabolites derivatized and extracted with the multi-device are graphically depicted in FIG. 2 and FIG. 3 showing the amino acids, the phospholipids and the acylcarnitines, respectively.

The quantities of the amono acids and acylcarnitine metabolites are shown in Table 3 below, also showing the accuracy and the variance of the values obtained using the multi-device.

TABLE 3

The quantities accuracy and reproducibility of the amino acids, lipids, lactate, creatinine and glucose from a single sample measured 10 times are shown in Table 3 and were obtained using the multi-device.

Amino Acids

| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [µmol/l] | std | CV [%] |
|---|---|---|---|---|---|---|---|---|---|---|---|---|---|---|
| Arginine-PTC | 64.8 | 71.0 | 67.5 | 68.7 | 62.3 | 63.1 | 67.9 | 65.6 | 67.4 | 66.5 | 63.7 | 66.2 | 2.6 | 4.0 |
| Phenylalanine-PTC | 74.0 | 71.6 | 72.1 | 81.5 | 70.1 | 69.2 | 70.4 | 73.6 | 72.5 | 72.9 | 76.2 | 73.1 | 3.4 | 4.7 |
| Proline-PTC | 114.4 | 117.1 | 124.5 | 120.4 | 120.2 | 120.6 | 137.2 | 118.2 | 127.5 | 126.3 | 120.6 | 122.5 | 6.2 | 5.1 |
| Lysine-PTC | 102.2 | 94.4 | 108.4 | 110.5 | 93.0 | 102.1 | 102.1 | 98.1 | 98.9 | 101.8 | 102.1 | 101.2 | 5.2 | 5.1 |
| Histidine-PTC | 90.0 | 97.0 | 95.4 | 89.4 | 93.0 | 89.2 | 97.7 | 82.5 | 88.5 | 95.3 | 100.6 | 92.6 | 5.2 | 5.6 |
| Tryptophane-PTC | 35.8 | 39.0 | 42.7 | 38.2 | 36.6 | 36.6 | 37.4 | 38.9 | 34.8 | 34.8 | 35.7 | 37.3 | 2.3 | 6.2 |
| Tyrosine-PTC | 93.4 | 99.9 | 95.7 | 92.7 | 94.8 | 103.7 | 95.2 | 97.2 | 86.1 | 87.4 | 83.6 | 93.6 | 6.0 | 6.4 |
| x-Leucine-PTC | 174.5 | 181.2 | 158.1 | 191.9 | 164.1 | 153.8 | 167.5 | 157.2 | 150.2 | 158.6 | 157.1 | 164.9 | 12.8 | 7.8 |
| Valine-PTC | 117.0 | 96.9 | 108.7 | 121.7 | 116.3 | 114.6 | 115.7 | 134.2 | 111.7 | 116.9 | 121.0 | 115.9 | 9.1 | 7.9 |
| Ornithine-PTC | 78.7 | 81.7 | 58.8 | 67.9 | 69.3 | 68.9 | 71.6 | 68.9 | 74.8 | 74.9 | 74.4 | 71.8 | 6.2 | 8.6 |
| Methionine-PTC | 44.4 | 38.2 | 34.9 | 41.5 | 44.7 | 38.8 | 37.8 | 43.2 | 36.2 | 36.0 | 36.3 | 39.3 | 3.6 | 9.1 |
| Citrulline-PTC | 28.3 | 24.8 | 28.0 | 23.5 | 20.6 | 25.2 | 26.1 | 25.0 | 28.0 | 29.4 | 25.8 | 25.9 | 2.5 | 9.7 |
| Glutamine-PTC | 455.8 | 455.6 | 445.7 | 364.4 | 352.0 | 369.0 | 374.2 | 322.0 | 355.7 | 369.1 | 385.1 | 385.1 | 45.6 | 11.8 |
| Serine-PTC | 182.1 | 153.7 | 176.7 | 177.1 | 191.9 | 188.5 | 173.4 | 137.8 | 132.6 | 134.0 | 154.9 | 163.9 | 22.1 | 13.5 |
| Threonine-PTC | 21.3 | 26.0 | 31.0 | 34.4 | 23.5 | 29.5 | 25.7 | 29.4 | 25.0 | 24.2 | 29.0 | 27.2 | 3.8 | 14.0 |
| Alanine-PTC | 219.6 | 316.7 | 227.8 | 282.3 | 298.7 | 267.5 | 205.8 | 177.8 | 203.0 | 245.4 | 210.9 | 241.4 | 44.4 | 18.4 |
| Asparagine-PTC | 236.4 | 250.9 | 204.5 | 179.4 | 168.4 | 136.5 | 170.1 | 192.4 | 230.5 | 206.7 | 157.0 | 193.9 | 35.7 | 18.4 |
| Glycine-PTC | 320.9 | 282.0 | 272.0 | 297.9 | 412.6 | 422.9 | 252.8 | 268.5 | 225.1 | 226.8 | 278.0 | 296.3 | 66.2 | 22.4 |
| Glutamic Acid-PTC | 2115.4 | 1508.6 | 1694.6 | 1220.8 | 2118.8 | 1560.0 | 2137.9 | 2770.8 | 2137.9 | 1563.6 | 1984.8 | 1892.1 | 431.0 | 22.8 |

Acylcarnitines

| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [µmol/l] | std | CV [%] |
|---|---|---|---|---|---|---|---|---|---|---|---|---|---|---|
| C2 | 8.487 | 9.674 | 9.529 | 9.007 | 8.845 | 9.105 | 9.847 | 9.477 | 9.928 | 8.552 | 9.137 | 9.24 | 0.49 | 5.4 |
| C18:1 | 0.161 | 0.233 | 0.218 | 0.216 | 0.193 | 0.193 | 0.207 | 0.225 | 0.205 | 0.191 | 0.180 | 0.20 | 0.02 | 10.4 |
| C8:1 | 0.161 | 0.233 | 0.218 | 0.216 | 0.193 | 0.193 | 0.207 | 0.225 | 0.205 | 0.191 | 0.180 | 0.20 | 0.02 | 10.4 |
| C0 | 38.351 | 48.949 | 51.179 | 53.867 | 53.869 | 52.218 | 61.745 | 60.195 | 56.018 | 52.762 | 56.524 | 53.24 | 6.21 | 11.7 |
| C12-DC | 0.021 | 0.015 | 0.017 | 0.013 | 0.015 | 0.017 | 0.015 | 0.017 | 0.016 | 0.017 | 0.017 | 0.02 | 0.00 | 12.4 |
| C14:2 | 0.041 | 0.050 | 0.044 | 0.035 | 0.047 | 0.052 | 0.041 | 0.050 | 0.035 | 0.047 | 0.045 | 0.04 | 0.01 | 13.1 |
| C8 | 0.232 | 0.306 | 0.352 | 0.274 | 0.200 | 0.212 | 0.264 | 0.250 | 0.258 | 0.276 | 0.299 | 0.27 | 0.04 | 16.4 |
| C12 | 0.043 | 0.051 | 0.071 | 0.047 | 0.043 | 0.043 | 0.044 | 0.048 | 0.046 | 0.045 | 0.055 | 0.05 | 0.01 | 16.7 |
| C12:1 | 0.028 | 0.025 | 0.030 | 0.031 | 0.027 | 0.035 | 0.035 | 0.030 | 0.040 | 0.034 | 0.019 | 0.03 | 0.01 | 18.6 |
| C16:1 | 0.038 | 0.016 | 0.036 | 0.037 | 0.030 | 0.035 | 0.030 | 0.033 | 0.024 | 0.030 | 0.035 | 0.03 | 0.01 | 20.2 |
| C3 | 0.293 | 0.401 | 0.524 | 0.376 | 0.274 | 0.324 | 0.309 | 0.435 | 0.423 | 0.473 | 0.423 | 0.39 | 0.08 | 20.5 |
| C14:1 | 0.110 | 0.106 | 0.103 | 0.113 | 0.113 | 0.141 | 0.174 | 0.118 | 0.172 | 0.108 | 0.117 | 0.13 | 0.03 | 20.6 |
| C4:1 | 0.110 | 0.106 | 0.103 | 0.113 | 0.113 | 0.141 | 0.174 | 0.118 | 0.172 | 0.108 | 0.117 | 0.13 | 0.03 | 20.6 |
| C7-DC | 0.050 | 0.036 | 0.044 | 0.052 | 0.040 | 0.039 | 0.066 | 0.055 | 0.036 | 0.064 | 0.041 | 0.05 | 0.01 | 22.5 |
| C5-M-DC | 0.192 | 0.204 | 0.184 | 0.202 | 0.191 | 0.209 | 0.210 | 0.316 | 0.177 | 0.136 | 0.160 | 0.20 | 0.05 | 22.7 |
| C4-OH | 0.106 | 0.080 | 0.100 | 0.167 | 0.138 | 0.129 | 0.170 | 0.151 | 0.175 | 0.115 | 0.121 | 0.13 | 0.03 | 23.7 |
| C11 | 0.006 | 0.008 | 0.010 | 0.010 | 0.013 | 0.008 | 0.010 | 0.007 | 0.012 | 0.008 | 0.006 | 0.01 | 0.00 | 23.9 |
| C16 | 0.136 | 0.204 | 0.188 | 0.169 | 0.127 | 0.096 | 0.132 | 0.137 | 0.100 | 0.124 | 0.178 | 0.14 | 0.04 | 24.6 |
| C4:1-DC | 0.148 | 0.182 | 0.241 | 0.167 | 0.111 | 0.097 | 0.165 | 0.146 | 0.226 | 0.127 | 0.218 | 0.17 | 0.05 | 28.3 |

Lipids

| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [µmol/l] | std | CV [%] |
|---|---|---|---|---|---|---|---|---|---|---|---|---|---|---|
| GPCho 36:3a | 190.12 | 219.29 | 195.68 | 224.00 | 250.66 | 236.77 | 231.16 | 199.46 | 207.93 | 210.60 | 198.76 | 214.9 | 19.2 | 8.9 |
| SM d18:1/16:0 | 311.11 | 387.86 | 330.25 | 339.33 | 346.71 | 381.94 | 419.57 | 307.61 | 337.20 | 348.34 | 380.74 | 353.7 | 34.8 | 9.8 |
| GPCho 36:2e | 22.84 | 25.00 | 20.99 | 22.67 | 21.71 | 21.29 | 23.19 | 23.91 | 27.44 | 19.20 | 21.12 | 22.7 | 2.2 | 9.9 |
| GPCho 32:1a | 55.79 | 50.54 | 58.33 | 55.17 | 58.33 | 67.42 | 64.89 | 62.50 | 67.03 | 56.25 | 48.00 | 58.6 | 6.4 | 10.9 |
| GPCho 32:0a | 7.69 | 7.37 | 7.73 | 5.20 | 7.87 | 6.71 | 7.82 | 6.63 | 7.74 | 9.23 | 7.07 | 7.4 | 1.0 | 13.6 |

-continued

| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [µmol/l] | std | CV [%] |
|---|---|---|---|---|---|---|---|---|---|---|---|---|---|---|
| LGPCho 18:2a | 6.17 | 6.43 | 6.17 | 6.00 | 8.55 | 6.45 | 6.52 | 4.35 | 7.93 | 7.28 | 6.21 | 6.6 | 1.1 | 16.7 |
| GPCho 34:1p | 76.84 | 76.34 | 87.50 | 93.10 | 73.96 | 82.02 | 80.85 | 127.50 | 82.42 | 83.33 | 82.00 | 86.0 | 14.7 | 17.2 |
| GPCho 36:1p | 243.16 | 268.82 | 354.16 | 327.59 | 300.00 | 277.53 | 288.30 | 425.00 | 290.11 | 269.79 | 259.00 | 300.3 | 51.8 | 17.3 |
| LGPCho 18:1p | 160.00 | 174.19 | 215.28 | 168.97 | 165.62 | 180.90 | 156.38 | 257.50 | 180.22 | 138.54 | 164.00 | 178.3 | 32.4 | 18.2 |
| LGPCho 18:0e | 40.24 | 47.37 | 51.38 | 43.35 | 47.19 | 65.10 | 53.63 | 59.64 | 50.97 | 67.69 | 37.88 | 51.3 | 9.7 | 18.8 |
| GPCho 38:1a | 18.95 | 21.51 | 29.17 | 17.24 | 25.00 | 22.47 | 28.72 | 25.00 | 26.37 | 25.00 | 34.00 | 24.9 | 4.8 | 19.3 |
| LGPCho 18:0p | 17.28 | 28.57 | 21.61 | 16.67 | 24.34 | 21.94 | 27.54 | 19.02 | 17.68 | 26.49 | 18.01 | 21.7 | 4.4 | 20.2 |
| GPCho 30:0a | 11.73 | 21.43 | 12.35 | 12.67 | 14.47 | 14.19 | 15.22 | 9.78 | 13.41 | 15.89 | 16.15 | 14.3 | 3.0 | 21.2 |
| GPCho 38:2a | 41.86 | 56.25 | 63.42 | 80.00 | 65.85 | 87.50 | 78.12 | 82.35 | 70.27 | 79.31 | 50.00 | 68.6 | 14.6 | 21.3 |
| GPCho 34:0e | 6.79 | 8.57 | 6.79 | 9.33 | 11.84 | 9.03 | 11.59 | 13.04 | 12.20 | 10.60 | 9.32 | 9.9 | 2.1 | 21.3 |
| GPCho 32:1p | 25.26 | 15.05 | 30.56 | 19.54 | 19.79 | 22.47 | 22.34 | 23.75 | 16.48 | 17.71 | 16.00 | 20.8 | 4.6 | 22.3 |
| GPIns 38:4 | 13.52 | 20.27 | 15.11 | 14.77 | 10.75 | 17.97 | 16.27 | 15.24 | 15.62 | 13.51 | 11.61 | 15.0 | 2.7 | 18.0 |
| GPIns 36:2 | 7.32 | 5.48 | 4.00 | 8.00 | 3.58 | 5.22 | 6.78 | 6.35 | 6.88 | 4.32 | 3.23 | 5.6 | 1.6 | 29.2 |

Lactate, Glucose and Creatinine

| Sample Name | QAlow C2 | QAlow C3 | QAlow C4 | QAlow C5 | QAlow C6 | QAlow C7 | QAlow C8 | QAlow C9 |
|---|---|---|---|---|---|---|---|---|
| Lactate | 21513 | 24282 | 25798 | 25443 | 22912 | 22519 | 23778 | 21673 |
| Glucose | 3826 | 4250 | 4383 | 4104 | 4235 | 4288 | 4486 | 4156 |
| Creatinine | 213.62 | 270.39 | 247.02 | 243.48 | 242.64 | 233.51 | 280.19 | 263.16 |

| Sample Name | QAlow C10 | QAlow C11 | QAlow C12 | mean [µmol/l] | std | CV [%] |
|---|---|---|---|---|---|---|
| Lactate | 22400 | 24968 | 23625 | 23537 | 1473 | 6.3 |
| Glucose | 3949 | 3983 | 3981 | 4149 | 202 | 4.9 |
| Creatinine | 262.74 | 238.50 | 244.91 | 249.1 | 18.7 | 7.5 |

Example 3

Therapeutic Drug Monitoring

Immunosuppressants are required to inhibit organ rejection after transplantation. The immunosuppressants used are Everolimus, Cyclosporin A, Tacrolimus, Sirolimus, and Mycophenolic acid. Therapeutic drug monitoring results prepared from a suitably prepared multi-device similarly as described above is shown here to further illustrate the use of the multi-device and support the claims of the invention.

Preparation and Conditions of Multi-Device

This multi-device was prepared with exactly the same method as described above, but instead using a single 8 mm cellulose spot (cut from generic card-10 539 859, Schlicher Schuell, Biosciences GmbH, Dassel, Germany) as the porous support.

Into the two multi-devices wells were placed a methanol solution (20 µl) containing Everolimus (200 ng/mL) (Sigma, Vienna, Austria), an internal standard for Sirolimus and Tacrolimus, and Cyclosporin D (400 ng/mL) (Sigma, Vienna, Austria), an internal standard for Cyclosporin A, was pipetted (Gilson 20 µl pipette) onto the porous supports of the multi-device and allowed to dry at room temperature for 30 minutes. Calibrator mixture and quality control levels I-V (whole blood calibrator set (level 0-6) for immunosuppressants, ClinChek R whole blood control for immunosuppressants, Recipe Chemicals and Instruments GmbH, Munich, Germany) were reconstituted according to manufactures instruction and both stored at −20° C. Prior to use, six calibrator solutions with increasing concentrations of Cyclosporin D and Everolimus and five quality control solution with various concentrations of Cyclosporin A, Tacrolimus, Sirolimus and Everolimus were thawed and allowed to reach room temperature around 23° C. Into six wells 20 µl of each six calibrators were pipetted (20 µl Gilson pipette) onto porous supports of multi-device. The five quality controls were pipetted into five separate wells porous supports of multi-device. To the multi-device was added acetonitrile (HPLC grade) immediately (Gilson 200 ml pipette) onto the multi-devices porous supports and instantly shaken with an orbital shaker at less than 600 rpm for 30 minutes. The eluant was collected by placing a 300 µl capacity microtiter capture plate under the device and then centriguation of the two at 500 g for 6 minutes. The eluant was then analyzed by mass spectrometric technique based on a published method (T. Koal, M. Deters, B. Casetta, V. Kaever, Simultaneous determination of four immunosuppressants by means of high speed and robust on-line solid phase extraction-high performance liquid chromatography-tandem mass spectrometry, J. Chromator. B, Analyt. Technol. Biomed. Life Sci. 2004 Jun. 15, 805(2); 215-222). A representative example of how the results are obtained and calculated are presented in FIG. 4 for Cyclosporin A analysis with LCMS to generate quantitative data. The areas under the integrated peaks of the internal standard Cyclosporin D were used for comparison against the area under the peak of the immunosuppressant Cyclosporin A in the five quality control samples containing known amounts.

FIGS. 5 to 8 show linear standard curves for all four immunosuppressants Cyclosporin A, Tacrolimus, Everolimus and Sirolimus using cellulose supports as inserts within the multi-device. Table 4 shows the calculated concentrations and the actual for accuracy comparisons of the five quality assurance materials analysed.

TABLE 4

| | | Analyte Concentration (ng/mL) | Calculated Concentration (ng/mL) | Accuracy (%) |
|---|---|---|---|---|
| Cyc A | Calibrator 0 | 0.2 | 0.201 | 101 |
| | Calibrator 1 | 46.7 | 43.8 | 93.7 |
| | Calibrator 2 | 115 | 116 | 101 |
| | Calibrator 3 | 304 | 315 | 103 |
| | Calibrator 4 | 483 | 472 | 97.7 |
| | Calibrator 5 | 777 | 820 | 106 |
| | Calibrator 6 | 1940 | 1900 | 97.9 |
| | QA1 | 61 | 45.3 | 74.2 |
| | QA2 | 116 | 95.5 | 82.3 |
| | QA3 | 254 | 220 | 86.7 |
| | QA4 | 474 | 391 | 82.6 |
| | QA5 | 1340 | 1310 | 98.1 |
| Tacrolimus | Calibrator 0 | 0.1 | No Peak | N/A |
| | Calibrator 1 | 2.1 | 2.17 | 103 |
| | Calibrator 2 | 5.6 | 5.38 | 96 |
| | Calibrator 3 | 10.9 | 10.5 | 95.9 |
| | Calibrator 4 | 15.8 | 16.1 | 102 |
| | Calibrator 5 | 21.9 | 22 | 101 |
| | Calibrator 6 | 38.8 | 38.9 | 100 |
| | QA1 | 3.23 | 3.69 | 114 |
| | QA2 | 6.6 | 7.35 | 111 |
| | QA3 | 13.2 | 14.8 | 112 |
| | QA4 | 0 | 0.246 | N/A |
| | QA5 | 0 | 0.355 | N/A |
| Sirolimus | Calibrator 0 | 0 | No Peak | N/A |
| | Calibrator 1 | 2.4 | 2.81 | 117 |
| | Calibrator 2 | 6.6 | 6.38 | 96.7 |
| | Calibrator 3 | 12.7 | 12.8 | 101 |
| | Calibrator 4 | 19.6 | 19.6 | 99.8 |
| | Calibrator 5 | 29 | 31.5 | 109 |
| | Calibrator 6 | 49.4 | 46.7 | 94.4 |
| | QA1 | 3.04 | 2.46 | 80.8 |
| | QA2 | 8.65 | 10.1 | 117 |
| | QA3 | 15.3 | 12.6 | 82.4 |
| | QA4 | 0 | No Peak | N/A |
| | QA5 | 0 | No Peak | N/A |
| Everolimus | Calibrator 0 | 0 | <0 | N/A |
| | Calibrator 1 | 2.1 | 2.46 | 117 |
| | Calibrator 2 | 6 | 5.71 | 95.1 |
| | Calibrator 3 | 12.3 | 12.5 | 101 |
| | Calibrator 4 | 18.2 | 18.3 | 100 |
| | Calibrator 5 | 25.3 | 27.1 | 107 |
| | Calibrator 6 | 46.5 | 44.4 | 95.5 |
| | QA1 | 3.48 | 3.18 | 91.3 |
| | QA2 | 11.1 | 10.8 | 97.3 |
| | QA3 | 18.2 | 18.5 | 102 |
| | QA4 | 0 | No Peak | N/A |
| | QA5 | 0 | No Peak | N/A |

Industrial Applicability

The invention makes possible a versatile and standardized analysis of various biofluids and tissues. For example, current in-house capacities can demonstrate simultaneous and fully automated sample preparation and analysis, generating more than 1000 quantitative and annotated data points from 10 µl of dried blood within 6 minutes of MS machine time covering various classes of metabolites within more than 100 annotated pathways. Thereby the invention for the first time overcomes most of the bottlenecks in (pre)analytics, automatization and data processing and interpretation that have prohibited so far wide-spread quantitative metabolomics mining.

Compared to related art analytical methods and devices, the quantitative analysis of the invention is extremely rugged and the results are highly reproducible. In particular, the metabolite data is much superior to comparable proteome or transcriptome data. Only 10 µl blood or serum or 20 µl urine or less than 100,000 cultured cells are needed.

The performance features of the analytical method and the device can meet both research (discovery) application and subsequently clinical diagnostic standards. This ensures or makes possible quality assured data, standardized data, which is comparable from laboratory to laboratory, rapid turnaround time, "ready to go" implementation (hits), easily received data interpretation and visualization and a very high degree in automatization and standardization (SOPs). The overall costs/data point makes the metabolome information orders of magnitudes less expensive than proteome information.

The quantitative information obtained by the method or the device of the invention covers pathways and metabolites in a systemic (system biology) context and scalable fashion. Thereby, a representative functional picture or screen shot or metabolic fingerprint of intermediary metabolism can be finally derived from arrays of marker metabolites.

Moreover, functional end-point information that is annotated and can conveniently be linked to information sources of the proteome, transcriptome and genome, recruiting metabolome information for system biology needs.

The device and the method can be used in an integrated tool (software and analytical) suitable to establish a new "standard" for simultaneous generation of large scale quantitative identified and annotated metabolite profiles and the study of complex and dynamic multiple biomaker patterns. Moreover, commercially available hardware components, consisting of a liquid handling system for automated and standardized sample preparation and a mass spectrometer for MS-MS analytics, can be integrated by proprietary and protected designed consumable-based products and application software, comprising (pre-) analytical procedures and innovative modules for quality controlled data processing, technical validation and documentation, statistical analysis and biochemical interpretation.

The sample preparation time in the invention (hit-based in batch of 90 samples/microtiter tray) is only roughly 2 h, and will be further reduced by means of parallalization through the scheduling software. A wide range of specific internal standards for quantification is pre-formulated in proprietary chemistry as integral part of usually one or two step reaction preparation and application hits, as is contained all necessary material for QC and QA in combination with software and SOPs.

Industrial applications include biomarker discovery and commercialization with the objective to utilize validated biomarkers for disease diagnosis, treatment efficacy or toxicity. The main applications in pharmaceutical development include the areas drug metabolism and pharmacokinetics, toxicology and safety, drug efficacy and pharmacodynamics. Other fields comprise clinical diagnostics and theranostics, where, for example, early, sensitive and specific diagnosis and accurate staging facilitates disease prevention instead of costly interventions and allows personalized treatment, and where therapeutic effects can be specifically monitored supporting personalized treatment. Further application areas include, but are not limited to, nutrition industry, wellness, homeland security, and basic biology.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. A device for the quantitative analysis of a drug and/or a metabolite profile in a biological sample, comprising:

(A) one or more wells,
(B) one or more inserts located in the wells, wherein the insert comprises:
  (a) a support comprising a sorbent material for liquids with which the support is impregnated, and
  (b) at least one organic internal standard being encapsulated with a covering material protecting the internal standard from degradation and chemical reactivity prior to use, wherein the covering material comprises at least one of a micelle-forming compound, a liposome-forming compound, a polyhydroxy compound, a polymer selected from polyalkylene glycol homopolymers or copolymers or mixtures thereof, and
(C) a retainer holding the insert within the well with a distance between the insert and the the walls and the bottom of the well in order to allow a free circulation of fluids around the insert.

2. The device according to claim 1, wherein the sorbent material comprises at least one of a cellulose material, glass fibres, glass beads, polyacrylamide gel, porous plastic inert polymer or porous graphite.

3. The device according to claim 1, wherein the encapsulated standard is microencapsulated.

4. The device according to claim 1, wherein the polymer is selected from a polyethylene glycol or polypropylene glycol homopolymer or copolymer or a mixture thereof.

5. The device according to claim 4, wherein the polymer is PEG 1000.

6. The device according to claim 1, wherein the polyhydroxy compound is selected from sorbitol or glycerol.

7. The device according to claim 1, wherein the micelle-forming compound is a surfactant.

8. The device according to claim 1, wherein the liposome forming compound is a phospholipid.

9. The device according to claim 8, wherein the phosopholipid is a phosphatidyl choline or a phosphatidyl ethanolamine or derivatives thereof.

10. The device according to claim 1, wherein the one or more wells comprise a filter for separating micron size solids, and an outlet for discharging the filtrate.

11. The device according to claim 10, wherein the filter is located between the insert and the outlet.

12. The device according to claim 10, wherein the outlet opens under applied centrifugal force or reduced pressure.

13. A device for the quantitative analysis of a drug and/or a metabolite profile in a biological sample, comprising:
(A) one or more wells;
(B) one or more inserts located in the wells, wherein the insert comprises
  (a) a support comprising a sorbent material for liquids which support is impregnated with
  (b) at least one organic internal standard; and
(C) a retainer holding the insert within the well with a distance between the insert and the walls and the bottom of the well in order to allow a free circulation of fluids around the insert.

14. The device according to claim 13, wherein the one or more wells comprise a filter for separating micron size solids, and an outlet for discharging the filtrate.

15. The device according to claim 14, wherein the filter is located between the insert and the outlet.

16. The device according to claim 14, wherein the outlet (5) opens under applied centrifugal force or reduced pressure.

17. A device for the quantitative analysis of a drug and/or a metabolite profile in a biological sample, comprising:
(A) one or more wells;
(B) one or more inserts located in the wells, wherein the insert comprises:
  (a) a support comprising a sorbent material for liquids which support is impregnated with
  (b) at least one organic internal standard being encapsulated with a covering material protecting the internal standard from degradation and chemical reactivity prior to use, wherein the covering material comprises at least one of a micelle-forming compound, a liposome-forming compound, a polyhydroxy compound, and a polymer selected from polyalkylene glycol homopolymers or copolymers or mixtures thereof; and
(C) a retainer holding the insert within the well with a distance between the insert and the the walls and the bottom of the well in order to allow a free circulation of fluids around the insert.

18. A kit for the quantitative analysis of a drug and/or a metabolite profile in a biological sample, comprising the device as defined in claim 1.

19. A kit for the quantitative analysis of a drug and/or a metabolite profile in a biological sample, comprising the device as defined in claim 13.

20. A kit for the quantitative analysis of a drug and/or a metabolite profile in a biological sample, comprising the device as defined in claim 17.

21. An apparatus for the quantitative analysis of a drug and/or a metabolite profile in a biological sample, comprising:
  (a) a treatment unit for preparing the drugs and/or metabolites to be screened comprising
    (a1) an automated liquid handling system, and
    (a2) at least one device as defined in claim 1 for derivatization of the drugs and/or metabolites present in the sample and for subsequent extraction of the derivatives;
  (b) a mass spectrometer for the quantitative targeted mass spectrometry-based analysis, and
  (c) a database for storing results of the analysis.

22. An apparatus for the quantitative analysis of a drug and/or a metabolite profile in a biological sample, comprising:
  (a) a treatment unit for preparing the drugs and/or metabolites to be screened comprising
    (a1) an automated liquid handling system, and
    (a2) at least one device as defined in claim 13 for derivatization of the drugs and/or metabolites present in the sample and for subsequent extraction of the derivatives;
  (b) a mass spectrometer for the quantitative targeted mass spectrometry-based analysis, and
  (c) a database for storing results of the analysis.

23. An apparatus for the quantitative analysis of a drug and/or a metabolite profile in a biological sample, comprising:
  (a) a treatment unit for preparing the drugs and/or metabolites to be screened comprising
    (a1) an automated liquid handling system, and
    (a2) at least one device as defined in claim 17 for derivatization of the drugs and/or metabolites present in the sample and for subsequent extraction of the derivatives;
  (b) a mass spectrometer for the quantitative targeted mass spectrometry-based analysis, and
  (c) a database for storing results of the analysis.

24. A device comprising:
a support comprising a sorbent material;
a plurality of mass spectrometry, organic, metabolite standards of known amounts impregnated in the support and dried; and
a well and a retainer, wherein the retainer holds the support within the well.

25. The device of claim 24, wherein the mass spectrometry, organic, metabolite standards comprise amino acids labelled with stable isotopes.

26. The device of claim 24, wherein the mass spectrometry, organic, metabolite standards comprise polypeptides labelled with stable isotopes.

27. The device of claim 24, wherein the mass spectrometry, organic, metabolite standards comprise lipids labelled with stable isotopes.

28. The device of claim 24, wherein the mass spectrometry, organic, metabolite standards comprise acylcarnitines labelled with stable isotopes.

29. A device for the quantitative analysis of a drug and/or a metabolite profile in a biological sample, comprising:
(A) one or more wells, wherein the one or more wells comprise a filter for separating micron size solids, and an outlet for discharging the filtrate; and
(B) one or more inserts located in the wells, wherein the insert comprises:
  (a) a support comprising a sorbent material for liquids with which the support is impregnated, and
  (b) at least one organic internal standard being encapsulated with a covering material protecting the internal standard from degradation and chemical reactivity prior to use, wherein the covering material comprises at least one of a micelle-forming compound, a liposome-forming compound, a polyhydroxy compound, a polymer selected from polyalkylene glycol homopolymers or copolymers or mixtures thereof, wherein the filter is located between the insert and the outlet.

30. A device for the quantitative analysis of a drug and/or a metabolite profile in a biological sample, comprising:
(A) one or more wells, wherein the one or more wells comprise a filter for separating micron size solids, and an outlet for discharging the filtrate and the outlet opens under applied centrifugal force or reduced pressure; and
(B) one or more inserts located in the wells, wherein the insert comprises:
  (a) a support comprising a sorbent material for liquids with which the support is impregnated, and
  (b) at least one organic internal standard being encapsulated with a covering material protecting the internal standard from degradation and chemical reactivity prior to use, wherein the covering material comprises at least one of a micelle-forming compound, a liposome-forming compound, a polyhydroxy compound, a polymer selected from polyalkylene glycol homopolymers or copolymers or mixtures thereof.

31. A device for the quantitative analysis of a drug and/or a metabolite profile in a biological sample, comprising:
(A) one or more wells,
(B) one or more inserts located in the wells, wherein the insert comprises:
  (a) a support comprising a sorbent material for liquids with which the support is impregnated, and
  (b) at least one organic internal standard being encapsulated with a covering material protecting the internal standard from degradation and chemical reactivity prior to use, wherein the covering material consists of at least one of a micelle-forming compound, a liposome-forming compound, a polyhydroxy compound, a polymer selected from polyalkylene glycol homopolymers or mixtures thereof.

* * * * *